(12) United States Patent
Roe et al.

(10) Patent No.: US 8,057,450 B2
(45) Date of Patent: Nov. 15, 2011

(54) ABSORBENT ARTICLE WITH SENSATION MEMBER

(75) Inventors: Donald Carroll Roe, West Chester, OH (US); Gregory Ashton, Cincinnati, OH (US); Jennifer Joan Nandrea, Cincinnati, OH (US); Masaharu Nishikawa, Montgomery, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 795 days.

(21) Appl. No.: 11/724,709

(22) Filed: Mar. 16, 2007

(65) Prior Publication Data
US 2007/0233025 A1    Oct. 4, 2007

Related U.S. Application Data

(60) Provisional application No. 60/788,505, filed on Mar. 31, 2006.

(51) Int. Cl.
*A61F 13/15* (2006.01)
*A61F 13/20* (2006.01)
(52) U.S. Cl. .................... 604/385.01; 604/367
(58) Field of Classification Search .......... 604/367, 604/385.01, 378
See application file for complete search history.

(56) References Cited

U.S. PATENT DOCUMENTS

| | | | |
|---|---|---|---|
| 3,848,594 A | 11/1974 | Buell | |
| 3,860,003 A | 1/1975 | Buell | |
| 3,881,491 A | 5/1975 | Whyte | |
| 3,911,173 A | 10/1975 | Sprague, Jr. | |
| 3,921,232 A | 11/1975 | Whyte | |
| 3,929,135 A | 12/1975 | Thompson | |
| 4,020,153 A | 4/1977 | Rowsell et al. | |
| 4,022,210 A | 5/1977 | Glassman | |
| 4,032,661 A | 6/1977 | Rowsell et al. | |
| 4,033,994 A | 7/1977 | Watson et al. | |
| 4,034,109 A | 7/1977 | Rowsell et al. | |
| 4,070,449 A | 1/1978 | Rowsell et al. | |
| 4,070,496 A | 1/1978 | Rowsell et al. | |
| 4,089,765 A | 5/1978 | Dudley | |
| 4,150,052 A | 4/1979 | Watson et al. | |
| 4,153,679 A | 5/1979 | Rowsell et al. | |
| 4,178,459 A | 12/1979 | Watson et al. | |
| 4,193,936 A | 3/1980 | Watson et al. | |
| 4,226,988 A | 10/1980 | Watson et al. | |

(Continued)

FOREIGN PATENT DOCUMENTS

EP    454105 B1    11/1995

(Continued)

OTHER PUBLICATIONS

U.S. Appl. No. 11/351,745, filed Feb. 10, 2006, Donald Roe.

(Continued)

*Primary Examiner* — Michele M Kidwell
(74) *Attorney, Agent, or Firm* — Laura L. Whitmer

(57) ABSTRACT

An absorbent article having a waist region and a crotch region. The article including a backsheet, an absorbent core, and a sensation member. The absorbent core is disposed between the backsheet and the sensation member. The sensation member forms a portion of a wearer-facing surface of the absorbent article. The sensation member has a wicking factor of greater than about 20 mm at about one minute, an absorptive capacity of greater than about 0.01 g/cm$^2$, and a capillary pressure of greater than about 50 mm of water.

31 Claims, 15 Drawing Sheets

U.S. PATENT DOCUMENTS

| | | | |
|---|---|---|---|
| 4,289,794 A | 9/1981 | Kleiner et al. | |
| 4,296,093 A | 10/1981 | Rowsell et al. | |
| 4,296,255 A | 10/1981 | Roswell et al. | |
| 4,324,246 A | 4/1982 | Mullane et al. | |
| 4,342,314 A | 8/1982 | Radel et al. | |
| 4,459,425 A | 7/1984 | Amano et al. | |
| 4,463,045 A | 7/1984 | Ahr et al. | |
| 4,515,595 A | 5/1985 | Kievit et al. | |
| 4,573,986 A | 3/1986 | Minetola et al. | |
| 4,609,518 A | 9/1986 | Curro et al. | |
| 4,610,678 A | 9/1986 | Weisman et al. | |
| 4,629,643 A | 12/1986 | Curro et al. | |
| 4,662,875 A | 5/1987 | Hirotsu et al. | |
| 4,673,402 A | 6/1987 | Weisman et al. | |
| 4,695,278 A | 9/1987 | Lawson | |
| 4,710,189 A | 12/1987 | Lash | |
| 4,785,996 A | 11/1988 | Ziecker et al. | |
| 4,795,454 A | 1/1989 | Dragoo | |
| 4,808,178 A | 2/1989 | Aziz et al. | |
| 4,816,025 A | 3/1989 | Foreman | |
| 4,834,735 A | 5/1989 | Alemany et al. | |
| 4,842,666 A | 6/1989 | Werenicz | |
| 4,846,815 A | 7/1989 | Scripps | |
| 4,888,231 A | 12/1989 | Angstadt | |
| 4,892,536 A | 1/1990 | Desmarais et al. | |
| 4,894,060 A | 1/1990 | Nestegard | |
| 4,909,803 A | 3/1990 | Aziz et al. | |
| 4,940,464 A | 7/1990 | Van Gompel et al. | |
| 4,946,527 A | 8/1990 | Battrell | |
| 4,963,140 A | 10/1990 | Robertson et al. | |
| 4,965,122 A | 10/1990 | Morman | |
| 4,968,312 A | 11/1990 | Khan | |
| 4,981,747 A | 1/1991 | Morman | |
| 4,990,147 A | 2/1991 | Freeland | |
| 5,006,394 A | 4/1991 | Baird | |
| 5,026,364 A | 6/1991 | Robertson | |
| 5,037,416 A | 8/1991 | Allen et al. | |
| 5,062,840 A | 11/1991 | Holt et al. | |
| 5,092,861 A | 3/1992 | Nomura et al. | |
| 5,116,662 A | 5/1992 | Morman | |
| 5,124,188 A | 6/1992 | Roe et al. | |
| 5,137,537 A | 8/1992 | Herron et al. | |
| 5,147,345 A | 9/1992 | Young et al. | |
| 5,151,092 A | 9/1992 | Buell et al. | |
| 5,156,793 A | 10/1992 | Buell et al. | |
| 5,167,897 A | 12/1992 | Weber et al. | |
| 5,171,236 A | 12/1992 | Dreier et al. | |
| 5,221,274 A | 6/1993 | Buell et al. | |
| 5,226,992 A | 7/1993 | Morman | |
| 5,246,433 A | 9/1993 | Hasse et al. | |
| 5,260,345 A | 11/1993 | Desmarais et al. | |
| 5,266,592 A | 11/1993 | Grub et al. | |
| 5,269,775 A | 12/1993 | Freeland et al. | |
| 5,306,266 A | 4/1994 | Freeland | |
| 5,318,555 A | 6/1994 | Siebers et al. | |
| 5,330,459 A | 7/1994 | Lavon et al. | |
| 5,336,545 A | 8/1994 | Morman | |
| 5,342,338 A | 8/1994 | Roe | |
| 5,342,343 A | 8/1994 | Kitaoka et al. | |
| 5,348,750 A | 9/1994 | Greenberg | |
| 5,380,313 A | 1/1995 | Goulait et al. | |
| 5,387,207 A | 2/1995 | Dyer et al. | |
| 5,397,316 A | 3/1995 | Lavon et al. | |
| 5,397,318 A | 3/1995 | Dreier | |
| 5,407,439 A | 4/1995 | Goulait | |
| 5,425,726 A | 6/1995 | Shimizu et al. | |
| 5,428,076 A | 6/1995 | Roe | |
| 5,460,622 A | 10/1995 | Dragoo et al. | |
| 5,509,915 A * | 4/1996 | Hanson et al. | 604/378 |
| 5,514,121 A | 5/1996 | Roe et al. | |
| 5,518,801 A | 5/1996 | Chappell et al. | |
| 5,540,671 A | 7/1996 | Dreier | |
| 5,540,673 A | 7/1996 | Thomas et al. | |
| 5,542,942 A | 8/1996 | Kline et al. | |
| 5,554,142 A | 9/1996 | Dreier et al. | |
| 5,554,143 A | 9/1996 | Roe et al. | |
| 5,554,145 A | 9/1996 | Roe et al. | |
| 5,567,609 A | 10/1996 | Sarras, Jr. et al. | |
| 5,569,233 A | 10/1996 | Goulait | |
| 5,569,234 A | 10/1996 | Buell et al. | |
| 5,571,096 A | 11/1996 | Dobrin et al. | |
| 5,580,411 A | 12/1996 | Nease et al. | |
| 5,607,760 A | 3/1997 | Roe | |
| 5,608,119 A | 3/1997 | Amano et al. | |
| 5,609,587 A | 3/1997 | Roe | |
| 5,625,222 A | 4/1997 | Yoneda et al. | |
| 5,635,191 A | 6/1997 | Roe et al. | |
| 5,643,588 A | 7/1997 | Roe et al. | |
| 5,649,914 A | 7/1997 | Glaug et al. | |
| 5,653,703 A | 8/1997 | Roe et al. | |
| 5,658,268 A | 8/1997 | Johns et al. | |
| 5,669,900 A | 9/1997 | Bullwinkel et al. | |
| 5,681,298 A | 10/1997 | Brunner et al. | |
| 5,702,376 A | 12/1997 | Glaug et al. | |
| H1732 H | 6/1998 | Johnson | |
| 5,797,892 A | 8/1998 | Glaug et al. | |
| 5,800,416 A * | 9/1998 | Seger et al. | 604/366 |
| 5,865,823 A | 2/1999 | Curro | |
| 5,883,028 A | 3/1999 | Morman et al. | |
| 5,885,264 A | 3/1999 | Matsushita | |
| 5,891,124 A | 4/1999 | Nomura et al. | |
| 5,897,545 A | 4/1999 | Kline et al. | |
| 5,938,648 A | 8/1999 | Lavon et al. | |
| 5,941,864 A | 8/1999 | Roe | |
| 5,947,947 A | 9/1999 | Tanzer et al. | |
| 5,957,908 A | 9/1999 | Kline et al. | |
| 5,968,025 A | 10/1999 | Roe et al. | |
| 5,977,430 A | 11/1999 | Roe et al. | |
| 5,989,380 A | 11/1999 | Frischer | |
| 5,997,520 A | 12/1999 | Ahr et al. | |
| 6,004,306 A | 12/1999 | Robles et al. | |
| 6,010,490 A | 1/2000 | Freeland et al. | |
| 6,013,063 A | 1/2000 | Roe et al. | |
| 6,107,535 A | 8/2000 | Rossini et al. | |
| 6,107,537 A | 8/2000 | Elder et al. | |
| 6,114,597 A | 9/2000 | Romare | |
| 6,118,041 A | 9/2000 | Roe et al. | |
| 6,120,487 A | 9/2000 | Ashton | |
| 6,120,488 A | 9/2000 | Vanrijswijck et al. | |
| 6,120,489 A | 9/2000 | Johnson et al. | |
| 6,120,783 A | 9/2000 | Roe et al. | |
| 6,146,367 A | 11/2000 | Otsubo et al. | |
| 6,153,209 A | 11/2000 | Vega et al. | |
| 6,156,024 A | 12/2000 | Schulte et al. | |
| 6,156,424 A | 12/2000 | Taylor | |
| 6,166,285 A | 12/2000 | Schulte et al. | |
| 6,168,584 B1 | 1/2001 | Allen et al. | |
| 6,169,225 B1 | 1/2001 | Otsubo | |
| 6,186,991 B1 | 2/2001 | Roe et al. | |
| 6,214,788 B1 | 4/2001 | Velazco et al. | |
| 6,229,063 B1 | 5/2001 | Shimoe et al. | |
| 6,253,159 B1 | 6/2001 | Bett et al. | |
| 6,264,641 B1 | 7/2001 | Van Gompel et al. | |
| 6,266,436 B1 | 7/2001 | Bett et al. | |
| 6,267,974 B1 | 7/2001 | Suares et al. | |
| 6,297,424 B1 | 10/2001 | Olson et al. | |
| 6,297,434 B1 | 10/2001 | Martello | |
| 6,307,119 B1 | 10/2001 | Cammarota et al. | |
| 6,313,372 B1 | 11/2001 | Suzuki | |
| 6,320,096 B1 | 11/2001 | Inoue et al. | |
| 6,328,982 B1 | 12/2001 | Shiroyama et al. | |
| 6,348,253 B1 * | 2/2002 | Daley et al. | 428/138 |
| 6,359,168 B1 | 3/2002 | Frerot et al. | |
| 6,428,526 B1 | 8/2002 | Heindel et al. | |
| 6,432,098 B1 | 8/2002 | Kline et al. | |
| 6,443,940 B1 | 9/2002 | Ashton et al. | |
| 6,444,064 B1 | 9/2002 | Henry et al. | |
| 6,448,467 B1 | 9/2002 | Herrlein et al. | |
| 6,465,073 B1 | 10/2002 | Morman et al. | |
| 6,479,154 B1 | 11/2002 | Walton et al. | |
| 6,482,191 B1 | 11/2002 | Roe et al. | |
| 6,503,236 B1 | 1/2003 | Uitenbroek et al. | |
| 6,548,431 B1 | 4/2003 | Bansal et al. | |
| 6,579,274 B1 | 6/2003 | Morman et al. | |
| 6,590,136 B1 | 7/2003 | Young et al. | |
| 6,592,884 B2 | 7/2003 | Hofmann et al. | |
| 6,617,016 B2 | 9/2003 | Zhang et al. | |

| Patent No. | Date | Inventor |
|---|---|---|
| 6,623,465 B1 | 9/2003 | Roe et al. |
| 6,623,837 B2 | 9/2003 | Morman et al. |
| 6,627,564 B1 | 9/2003 | Morman et al. |
| 6,627,786 B2 | 9/2003 | Roe et al. |
| 6,635,797 B2 | 10/2003 | Olson et al. |
| 6,642,427 B2 | 11/2003 | Roe et al. |
| 6,676,646 B2 | 1/2004 | Bast et al. |
| 6,680,265 B1 | 1/2004 | Smith et al. |
| 6,680,422 B2 | 1/2004 | Roe |
| 6,692,475 B2 | 2/2004 | Mishima |
| 6,702,795 B2 | 3/2004 | Klemp |
| 6,716,441 B1 | 4/2004 | Osborne et al. |
| 6,726,668 B2 | 4/2004 | Underhill et al. |
| 6,727,404 B2 | 4/2004 | Ruman et al. |
| 6,743,314 B2 | 6/2004 | Henry et al. |
| 6,766,817 B2 | 7/2004 | da Silva |
| 6,811,865 B2 | 11/2004 | Morman et al. |
| 6,849,324 B2 | 2/2005 | Meece et al. |
| 6,875,710 B2 | 4/2005 | Eaton et al. |
| 6,881,206 B2 | 4/2005 | Underhill et al. |
| 6,884,906 B2 | 4/2005 | Dewis et al. |
| 6,905,488 B2 | 6/2005 | Olson |
| 6,909,028 B1 | 6/2005 | Shawver et al. |
| 6,918,404 B2 | 7/2005 | da Silva |
| 6,929,819 B2 | 8/2005 | Underhill et al. |
| 6,943,894 B2 | 9/2005 | Kitahara |
| 6,955,733 B2 | 10/2005 | Miller et al. |
| 6,957,160 B2 | 10/2005 | Miller et al. |
| 6,958,432 B2 | 10/2005 | Underhill et al. |
| 6,960,834 B2 | 11/2005 | Nakamura et al. |
| 7,002,055 B2 | 2/2006 | Long et al. |
| 7,033,341 B2 | 4/2006 | Mishima |
| 7,056,411 B2 | 6/2006 | Desai et al. |
| 7,066,586 B2 | 6/2006 | da Silva |
| 7,123,981 B2 | 10/2006 | Dollevoet et al. |
| 7,169,137 B2 | 1/2007 | Shimada |
| 7,195,729 B2 | 3/2007 | Jackson et al. |
| 7,223,818 B2 | 5/2007 | Autran et al. |
| 7,285,255 B2 | 10/2007 | Kadlec et al. |
| 7,301,036 B2 | 11/2007 | Parmee et al. |
| 2002/0062117 A1 | 5/2002 | Raufman et al. |
| 2002/0111596 A1 | 8/2002 | Fletcher et al. |
| 2002/0138062 A1 | 9/2002 | Kuen et al. |
| 2003/0060794 A1 | 3/2003 | Olson |
| 2003/0065298 A1 | 4/2003 | Krishnaswamy Mirle et al. |
| 2003/0077430 A1 | 4/2003 | Grimm et al. |
| 2003/0087059 A1 | 5/2003 | Jackson et al. |
| 2003/0088220 A1 | 5/2003 | Molander et al. |
| 2003/0091807 A1 | 5/2003 | Desai et al. |
| 2003/0114807 A1 | 6/2003 | Underhill et al. |
| 2003/0114821 A1 | 6/2003 | Underhill et al. |
| 2003/0120240 A1 | 6/2003 | Buell et al. |
| 2003/0125682 A1 | 7/2003 | Olson et al. |
| 2003/0125689 A1 | 7/2003 | Olson et al. |
| 2003/0162458 A1 | 8/2003 | Tsujiyama et al. |
| 2003/0167049 A1 | 9/2003 | Gibbs |
| 2003/0193113 A1 | 10/2003 | Glovatsky |
| 2003/0199845 A1 | 10/2003 | Roe et al. |
| 2003/0233082 A1 | 12/2003 | Kline et al. |
| 2004/0067970 A1 | 4/2004 | Foster et al. |
| 2004/0071780 A1 | 4/2004 | Lillard et al. |
| 2004/0081680 A1 | 4/2004 | Pesce et al. |
| 2004/0082654 A1 | 4/2004 | Pesce et al. |
| 2004/0092902 A1 | 5/2004 | Hoffman et al. |
| 2004/0110442 A1 | 6/2004 | Rhim et al. |
| 2004/0127876 A1 | 7/2004 | Stevens |
| 2004/0132374 A1 | 7/2004 | Kobayashi |
| 2004/0162536 A1 | 8/2004 | Becker et al. |
| 2004/0167486 A1 | 8/2004 | Busam et al. |
| 2004/0191279 A1 | 9/2004 | Klofta |
| 2004/0193133 A1 | 9/2004 | Desai et al. |
| 2004/0211696 A1 | 10/2004 | Underhill et al. |
| 2004/0220540 A1 | 11/2004 | Underhill et al. |
| 2004/0254549 A1 | 12/2004 | Olson et al. |
| 2004/0254550 A1 | 12/2004 | Huang et al. |
| 2005/0027274 A1 | 2/2005 | Suzuki et al. |
| 2005/0049553 A1 | 3/2005 | Triplett et al. |
| 2005/0049568 A1 | 3/2005 | Underhill et al. |
| 2005/0096612 A1* | 5/2005 | Davis et al. .......... 604/361 |
| 2005/0096618 A1 | 5/2005 | Magee et al. |
| 2005/0106980 A1 | 5/2005 | Abed et al. |
| 2005/0124952 A1 | 6/2005 | Zehner et al. |
| 2005/0125877 A1 | 6/2005 | Benjamin et al. |
| 2005/0125923 A1 | 6/2005 | Benjamin et al. |
| 2005/0129743 A1 | 6/2005 | Benjamin et al. |
| 2005/0139713 A1 | 6/2005 | Weber et al. |
| 2005/0147785 A1 | 7/2005 | Ahn et al. |
| 2005/0177123 A1 | 8/2005 | Catalan |
| 2005/0214461 A1 | 9/2005 | Desai et al. |
| 2005/0222546 A1 | 10/2005 | Vargo et al. |
| 2006/0025737 A1 | 2/2006 | Song et al. |
| 2006/0212010 A1 | 9/2006 | Roe |
| 2006/0212018 A1 | 9/2006 | Roe |
| 2006/0224132 A1 | 10/2006 | Roe et al. |
| 2006/0247594 A1 | 11/2006 | Nickel et al. |
| 2007/0032766 A1 | 2/2007 | Liu |
| 2007/0049884 A1 | 3/2007 | Long et al. |
| 2007/0073261 A1 | 3/2007 | Ashton et al. |
| 2007/0191797 A1* | 8/2007 | Roe et al. .......... 604/361 |
| 2007/0287982 A1 | 12/2007 | Lodge et al. |
| 2007/0287983 A1 | 12/2007 | Lodge et al. |

FOREIGN PATENT DOCUMENTS

| | | |
|---|---|---|
| EP | 547497 | 6/1997 |
| EP | 0 937 446 A2 | 8/1999 |
| EP | 1 287 799 A2 | 3/2003 |
| WO | WO-94/14395 A1 | 7/1994 |
| WO | WO-95/16746 | 6/1995 |
| WO | WO-02/091968 A2 | 11/2002 |
| WO | WO-2004/071780 A2 | 8/2004 |
| WO | WO-2005/041834 A1 | 5/2005 |
| WO | WO-2005/102239 A1 | 11/2005 |
| WO | WO-2006 017518 A2 | 2/2006 |

OTHER PUBLICATIONS

U.S. Appl. No. 11/724,713, filed Mar. 16, 2007, Donald Roe.
U.S. Appl. No. 11/724,851, filed Mar. 16, 2007, Donald Roe.
U.S. Appl. No. 11/724,922, filed Mar. 16, 2007, Donald Roe.
U.S. Appl. No. 11/724,838, filed Mar. 16, 2007, Donald Roe.
PCT Search Report mailed Aug. 23, 2006 (4 pages).
"Pampers Ultra Trainers" package, Size 3 from Finneytown Kroger's dated Oct. 3, 1998. 2 pages.
Timothy R. Schum, MD, et al.—Sequential Acquisition of Toilet-Training Skills: A Descriptive Study of Gender and Age Differences in Normal Children, *Pediatrics*, Mar. 2002, 7 pages vol. 109, No. 3.

* cited by examiner

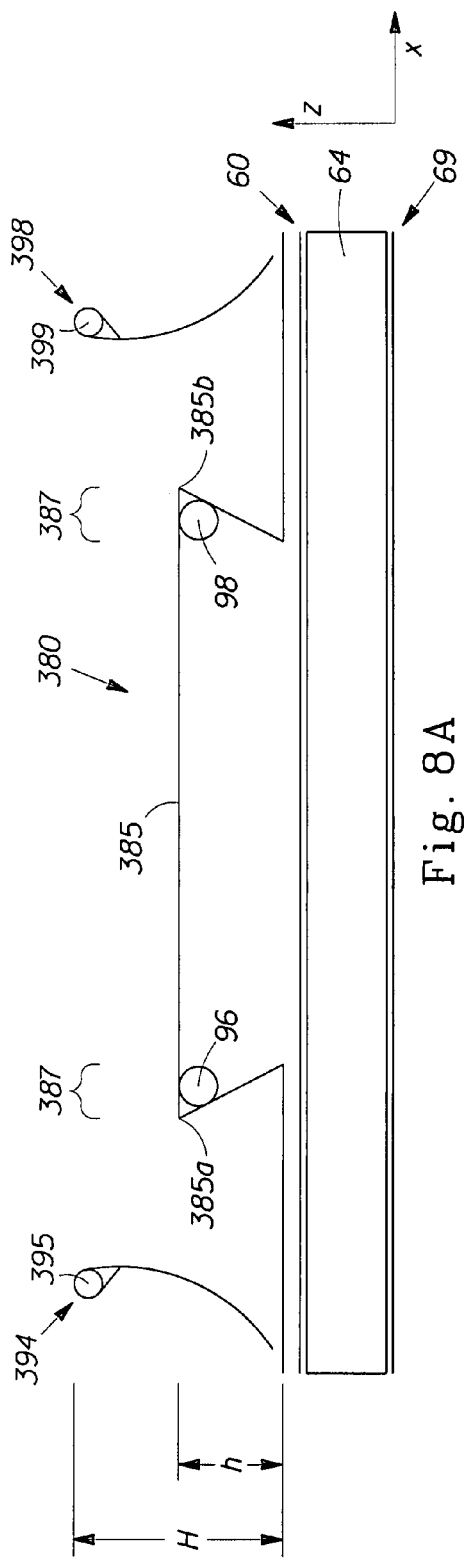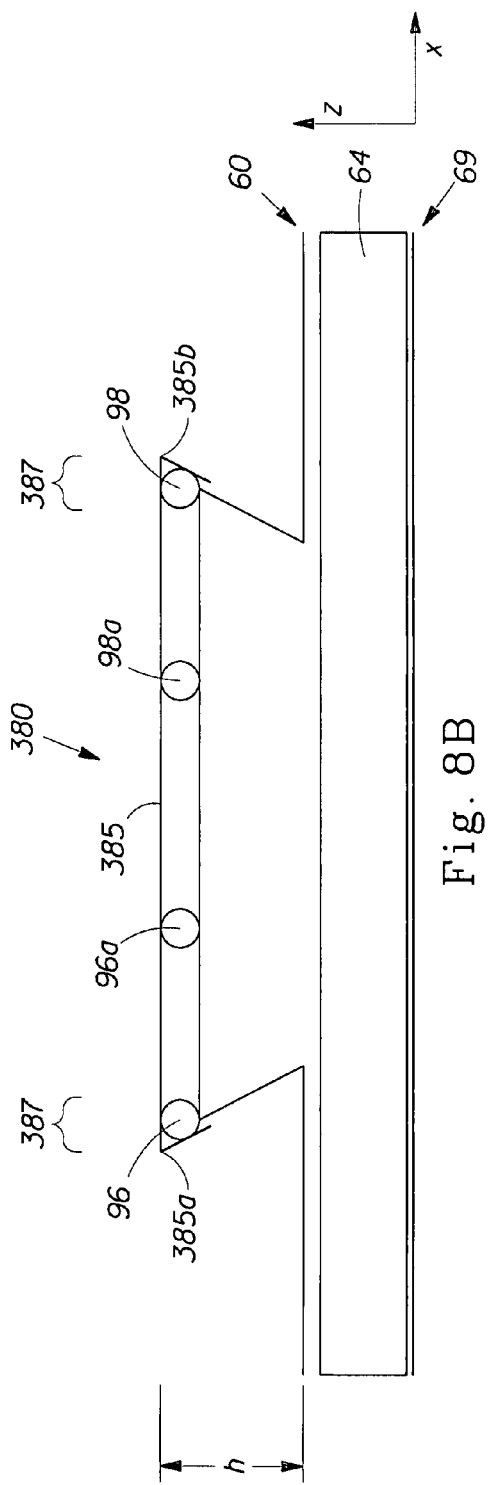

ABSORBENT ARTICLE WITH SENSATION MEMBER

CROSS REFERENCE TO RELATED APPLICATION

This application claims the benefit of U.S. Provisional Application No. 60/788,505, filed Mar. 31, 2006, the substance of which is incorporated herein by reference.

FIELD OF THE INVENTION

The present disclosure generally relates to absorbent articles, including diapers, training pants, pull-on diapers, absorbent inserts, diaper holders and liners, and the like, and in particular to an absorbent article with a sensation member, which may be adapted for use in urinary toilet training.

BACKGROUND OF THE INVENTION

Absorbent articles are well known in the art. These articles typically have an absorbent assembly which captures and absorbs bodily exudates discharged from the wearer. Typical absorbent articles include a topsheet facing the wearer, which permits fluid exudates to pass through, and a backsheet, which prevents the exudates from escaping from the absorbent article.

The toilet training stage may be referred to as the "point of exit" from the diaper product category because toddlers who have successfully completed toilet training typically no longer wear diapers. The age at which children are toilet trained in "developed" countries has increased steadily over the past several decades and is now, generally, in the range of about 24-48 months. One reason for which toilet training has become delayed is that significant technical improvements have been made in diaper dryness and comfort. For example, when wearing a typical modern diaper, the child may have dry skin even after one or more occurrences of urination. As a result, the child may feel little or no discomfort and often may not even be aware that he or she has urinated.

It is believed that if a signal were provided to the wearer upon urination, the signal could help in training the wearer. For example, the signal could provide slight discomfort to the wearer thereby alerting the wearer that he or she has urinated. There are disposable articles commercially available which provide feedback to the wearer upon urination.

However, it has been found during development of the present invention that several—sometimes contradictory—characteristics of feedback mechanisms are important. For example, it has been found during development of the present invention that an ideal feedback mechanism should ideally provide a temporary signal. The temporary duration of the signal helps to reinforce the association with the urination event. In other words, if the signal lasts too long or indefinitely the wearer may become undesirably accustomed to the signal. Additionally, a signal which persists may lead to undesirable impacts such as stress on the wearer's skin.

Another characteristic of well designed feedback mechanisms discovered during development of the present invention is that such mechanisms should be harmless to the wearer and the wearer's skin. For example, a feedback mechanism which provided prolonged contact of a urine saturated component with the skin could lead to skin irritation and, therefore, would not be ideal.

It has also been found during development of the present invention that ideal feedback mechanisms be unmistakable to the wearer. For example, if the signal provided to the wearer were too subtle or ambiguous the training benefit of the signal may not be effectively achieved.

Consequently, a need, therefore, exists for disposable absorbent articles and garments which provide urination feedback mechanisms which are as immediate and unmistakable to the wearer as possible. Such feedback mechanisms should also be temporary and harmless. It would be desirable to provide an article that can facilitate urinary toilet training by enhancing a wearer's awareness that urination has occurred by providing such a signal to the wearer while at the same time providing the protection of an absorbent article to prevent soiling of the wearer's clothing and surroundings.

SUMMARY OF THE INVENTION

An absorbent article constructed in accordance with the present invention may provide a wearer with immediate and unmistakable feedback indicating to the wearer when he or she has urinated. Additionally, an absorbent article constructed in accordance with the present invention may provide the wearer with feedback which is temporary and harmless to the wearer.

In some embodiments, an absorbent article constructed in accordance with the present invention may comprise a waist region and a crotch region. The absorbent article may further comprise a backsheet, a sensation member, and an absorbent core disposed between the backsheet and the sensation member. The sensation member may form a portion of a wearer-facing surface of the absorbent article. Additionally, the sensation member may have a wicking factor of greater than about 20 mm at about one minute, an absorptive capacity of greater than about 0.01 g/cm$^2$, and a capillary pressure of greater than about 50 mm of water.

In some embodiments, a disposable diaper for wearer about the lower torso of a wearer may be constructed in accordance with the present invention. The disposable diaper may have a first waist region disposed adjacent to a first waist edge, a second waist region disposed adjacent to a second waist edge, and a crotch region disposed between the first waist region and the second waist region. The disposable diaper may further comprise a first longitudinal edge and a second longitudinal edge; a topsheet, a backsheet, and an absorbent core disposed between the topsheet and the backsheet.

The disposable diaper may further comprise a first side panel extending outward from the first longitudinal edge in the first waist region and a second side panel extending outward from the second longitudinal edge in the first waist region, wherein the first side panel and the second side panel are adaptable to engage the second waist region thereby forming a waist opening and a pair of leg openings. Additionally, the disposable diaper may further comprise a sensation member disposed adjacent to the topsheet, wherein the sensation member has a wicking factor of greater than about 20 mm at about one minute, an absorptive capacity of greater than about 0.01 g/cm$^2$, and a capillary pressure of greater than about 50 mm of water.

BRIEF DESCRIPTION OF THE DRAWINGS

While the specification concludes with claims particularly pointing out and distinctly claiming the subject matter that is regarded as the present invention, it is believed that the invention will be more fully understood from the following description taken in conjunction with the accompanying drawings. In the accompanying drawing figures, like reference numerals identify like elements, which may or may not be identical in the several exemplary embodiments that are depicted. Some of the figures may have been simplified by the omission of selected elements for the purpose of more clearly showing other elements. Such omissions of elements in some figures are not necessarily indicative of the presence or absence of particular elements in any of the exemplary embodiments, except as may be explicitly delineated in the corresponding written description. None of the drawings are necessarily to scale.

FIGS. 8A-8C are cross-sectional views of another embodiment of an absorbent article.

DETAILED DESCRIPTION OF THE INVENTION

Figure 1A:
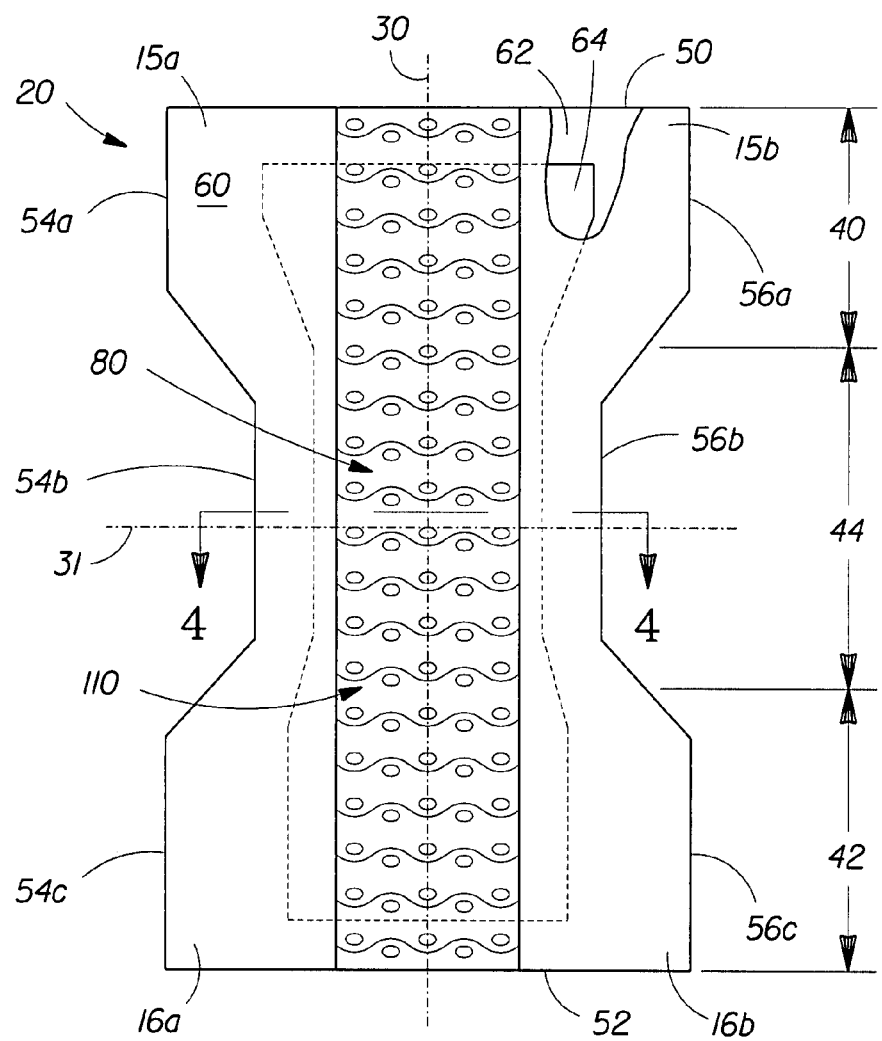
FIG. 1A is a plan view showing an absorbent article with a section of a topsheet removed to expose an underlying absorbent core and highlighting a sensation member.

Definitions:

As used herein, the following terms have the following meanings:

The term "absorbent article" refers to a device that absorbs and contains liquid, and more specifically, refers to a device that is placed against or in proximity to the body of the wearer to absorb and contain the various exudates discharged from the body.

"Body-facing", "wearer-facing", "outer-facing", and "garment-facing", refer respectively to the relative location of an element or a surface of an element or group of elements. "Body-facing" and "wearer-facing" imply the element or surface is nearer to the wearer during wear than some other element or surface. "Garment-facing" and "outer-facing" imply the element or surface is more remote from the wearer during wear than some other element or surface (i.e., element or surface is proximate to the wearer's garments that may be worn over the disposable absorbent article).

The term "diaper" refers to an absorbent article generally worn by infants and incontinent persons about the lower torso and having the general form of a sheet, different portions of which are fastened together to encircle the waist and the legs of the wearer.

The term "disposable" refers to absorbent articles that generally are not intended to be laundered or otherwise restored or reused as absorbent articles, i.e., they are intended to be discarded after use and, preferably, to be recycled, composted or otherwise disposed of in an environmentally compatible manner.

As used herein "elastically extensible" refers to characteristics of extensible materials that have the ability to return to approximately their original dimensions after a force that extended the extensible material is removed. Herein, any material or element described as "extensible" may also be "elastically extensible" unless otherwise provided.

The term "graphic" refers to a product of graphic art or a graphic representation in a pictorial form. A graphic may be a symbol, shape, image, text, or other form of indicia. Examples of "graphics" are provided in U.S. Patent Publication No. 2005/0129743A1, U.S. Patent Publication No. 2005/0125923A1, and U.S. Patent Publication No. 2005/0125877A1.

As used herein the term "joined" encompasses configurations whereby an element is directly secured to another element by affixing the element directly to the other element, and configurations whereby an element is indirectly secured to another element by affixing the element to an intermediate member(s) which in turn are affixed to the other element.

The term "lateral" or "transverse" refers to a direction running at a 90 degree angle to the longitudinal direction and includes directions within ±45 degrees of the lateral direction.

The term "longitudinal" refers to a direction running parallel to the maximum linear dimension of the article and includes directions within ±45 degrees of the longitudinal direction.

The terms "pant", "training pant", "closed diaper", "pre-fastened diaper", and "pull-on diaper", as used herein, refer to disposable garments having a waist opening and leg openings designed for infant or adult wearers. A pant can be configured such that the pant has a closed waist and leg openings prior to being donned on the wearer, or the pant can be configured such that the waist is closed and the leg openings formed while on the wearer. A pant may be preformed by any suitable technique including, but not limited to, joining together portions of the article using refastenable and/or non-refastenable bonds (e.g., seam, weld, adhesive, cohesive bond, fastener, etc.). A pant may be preformed anywhere along the circumference of the article (e.g., side fastened, front waist fastened, rear waist fastened). Examples of suitable pants are disclosed in U.S. Pat. Nos. 5,246,433; 5,569,234; 6,120,487; 6,120,489; 4,940,464; 5,092,861; 5,897,545; 5,957,908; and U.S. Patent Publication No. 2003/0233082 A1.

The terms "permeable" and "impermeable" refer to the penetrability of materials in the context of the intended usage of disposable absorbent articles. Specifically, the term "permeable" refers to a layer or a layered structure having pores, openings, and/or interconnected void spaces that permit liquid water to pass through its thickness in the absence of a forcing pressure. Conversely, the term "impermeable" refers to a layer or a layered structure through the thickness of which liquid water cannot pass in the absence of a forcing pressure. A layer or a layered structure that is "impermeable" according to this definition may be permeable to water vapor, i.e., may be "vapor-permeable". Such a "vapor-permeable" layer or layered structure is commonly known in the art as "breathable". As is well known in the art, a common method for measuring the permeability to water of the materials typically used in absorbent articles is a hydrostatic pressure test, also called a hydrostatic head test or simply a "hydrohead" test. Suitable well known compendial methods for hydrohead testing are approved by. INDA (formerly the International Nonwovens and Disposables Association, now The Association of the Nonwoven Fabrics Industry) and EDANA (European Disposables And Nonwovens Association).

The term "x-y plane" refers to the generally planar structure of a sheet-material defined by its length and width and lies between the sheet material's two major surfaces regardless of whether or not the sheet material is flat or curved.

The term "z-direction" refers to the direction through the thickness of a sheet material and generally orthogonal to the x-y plane.

The term "sensory element member" is analogous to "sensation member" and "feedback response member" as used herein or in copending applications all filed on Mar. 31, 2006.

Description:

A disposable absorbent article constructed in accordance with the present invention comprises a sensation member which is capable of providing a feedback response to the wearer indicating to the wearer that he or she has urinated. The feedback response provided by the sensation member of the disposable absorbent article can be immediate and unmistakable to the wearer.

The sensation member of the present invention may provide a feedback response to the wearer upon a urination event by the wearer. The type of feedback response provided may vary, but may include, by way of example, a wetness sensation response, a temperature response, or a combination thereof. A temperature response could include one or both of an actual temperature change produced in the article which is transmitted to the wearer's skin or a sensation of warmness or coolness produced without an actual temperature change. Temperature changes can include increases (i.e. warmness) or decreases (i.e. coolness) from the initial or "baseline" temperature, for example the temperature of the urine as excreted from the body, prior to the onset of the response. As another example, in some embodiments, a sensation member may provide a wetness signal upon being wetted and also provide a temperature change as a portion of the liquid evaporates from the sensation member. The sensation member can be disposed within an absorbent article such that the sensation member forms a portion of a wearer-facing surface of the absorbent article.

As shown in FIG. 1A, in some embodiments, an absorbent article 20 may comprise a first waist region 40, a second waist region 42, and a crotch region 44 disposed between the first waist region 40 and the second waist region 42. The waist regions 40 and 42 generally comprise those portions of the absorbent article 20 which, when worn, can surround the waist of the wearer. The waist regions 40 and 42 may include elastic elements such that they gather about the waist of the wearer to provide improved fit and containment. The crotch region 44 is that portion of the absorbent article 20 which, when the disposable absorbent article 20 is worn, is generally positioned between the legs of the wearer.

The absorbent article 20 has a first waist edge 50 in the first waist region 40 and a second waist edge 52 in the second waist region 42. The first waist edge 50 and the second waist edge 52 can be generally parallel to a lateral axis 31 of the absorbent article 20. The absorbent article 20 further comprises a first side edge 54 and a second side edge 56. The first and second side edges 54 and 56 can be generally parallel to a longitudinal axis 30 and extend between the first waist edge 50 and the second waist edge 52. The portion of the first side edge 54 in the first waist region 40 is designated 54A, the portion in the crotch region 44 is designated 54B, and the portion in the second waist region 42 is designated 54C. The corresponding portions of the second side edge 56 are designated 56A, 56B, and 56C, respectively.

The absorbent article 20 preferably comprises a topsheet 60, a backsheet 62, and an absorbent core 64, which may be disposed between the topsheet 60 and the backsheet 62 with the topsheet 60 attached to the backsheet 62. The topsheet 60 may be fully or partially elasticized or may be foreshortened so as to provide a void space between the topsheet 60 and the core 64. As explained below, a fully or partially elasticized topsheet 60 may also to tend to draw a sensation member against the skin of the wearer. Exemplary structures including elasticized or foreshortened topsheets are described in greater detail in U.S. Pat. Nos. 4,892,536, 4,990,147, 5,037,416, and 5,269,775, among others.

The absorbent article 20 may further comprise ear panels 15A, 15B, 16A, and 16B, which extend laterally outward. The ear panels 15A and 15B may comprise the portions of the side edge 54A and 56A, respectively. The ear panels 16A and 16B may comprise the portions of the side edge 54C and 56C, respectively. The ear panels 15A, 15B, 16A, and/or 16B, in some embodiments, can be elastically extensible.

The ear panels 15A, 15B, 16A, and 16B, are those portions of the disposable absorbent article 20 which tend to be disposed on the outer surface of the leg of a wearer during use. In contrast, the crotch region 44 of the disposable absorbent article is that portion of the disposable absorbent article which tends to be disposed on the inner surface of the leg of the wearer during use.

In some embodiments, the ear panel 1SA can be joined to the ear panel 16A in a non-refastenable manner or in a refastenable manner such that the first waist region 40 and the second waist region 42 are joined. The ear panels 15B and 16B can be joined together in a similar fashion as that described for ear panels 15A and 16A. In some embodiments, the absorbent article 20 or a plurality thereof can be sold pre-fastened in a package. The pre-fastened absorbent articles 20 may comprise ear panels which are joined non-refastenably and/or refastenably. In some embodiments, a plurality of absorbent articles 20 can be sold in a package wherein some of the disposable absorbent articles are pre-fastened and some are not pre-fastened.

Although not shown, the ear panels 15A, 15B, 16A, and/or 16B, may comprise fastening elements. Any suitable fastening element known in the art can be used in the present invention. Examples of suitable fastening elements include engaging components, receiving components, adhesive components, cohesive components, the like, or any suitable combination thereof.

An example of a suitable engaging component may comprise hook fastening material. A hook fastening material according to the present invention may be manufactured from a wide range of materials. Examples of suitable materials include nylon, polyester, polypropylene, or any combination of these materials, or other materials as are known in the art. An exemplary hook fastening material is described in U.S. Pat. No. 4,846,815. Other suitable examples and processes for making the same are described in U.S. Pat. No. 5,540,673 and in WO 2004/082918. Alternatively, the engaging elements may have any shape such as hooks, "T's", mushrooms, or any other shape as are well known in the art.

An example of a suitable receiving component may comprise a plurality of loops. Loop fastening material and a method for making the same are described in U.S. Pat. Nos. 5,380,313; 5,569,233; 5,407,439; 5,542,942; 5,669,900; 5,318,555; U.S. Application Publication No. 2003/0077430; and WO 04/030763.

An example of a suitable adhesive component may comprise discrete tape tabs. An example of a suitable tape tab is available from the 3M Corporation of St. Paul, Minn., U.S.A. under the designation of XMF99121. Any suitable adhesive component known in the art can be used.

An example of a suitable cohesive component may comprise cohesive fastening patches. In some embodiments, the cohesive fastening patches may be formed of an inherently crystalline water-based synthetic elastomer to which a tackifying agent has been added to disrupt the polycrystalline structure and thereby render the elastomer cohesive. Exemplary synthetic cohesive products are available from Andover Coated Products, Incorporated, of Salisbury, Mass., U.S.A. and are described in U.S. Pat. No. 6,156,424.

Other exemplary fasteners and fastener arrangements, the fastening components forming these fasteners, and the materials that are suitable for forming fasteners are described in U.S. Application Publication Nos. 2003/0060794 and 2005/0222546 and U.S. Pat. No. 6,428,526, among others. Additionally, other examples of suitable fasteners include macrofasteners which are described in U.S. Pat. No. 6,432,098 and in U.S. Patent Application Publication No. 2003/0233082A1.

It has been discovered during development of the present invention that the development of dressing and undressing skills as well as the development of continence are both related to and potentially important to a successful potty training experience. For example, a child may begin to recognize the urge to urinate and have an ability to control and delay the onset of urination. If such a child has a desire to use the toilet, but is wearing a disposable absorbent article which he or she does not have the dexterity to remove readily, the child may not be able to use the toilet successfully. Therefore, it may be desirable to provide "easy open" features, such as those described further below either with or without refastenability features in a garment in combination with the sensory elements described herein to provide a garment having multiple potty training features in combination which synergistically re-enforce each other.

Figure 1B:
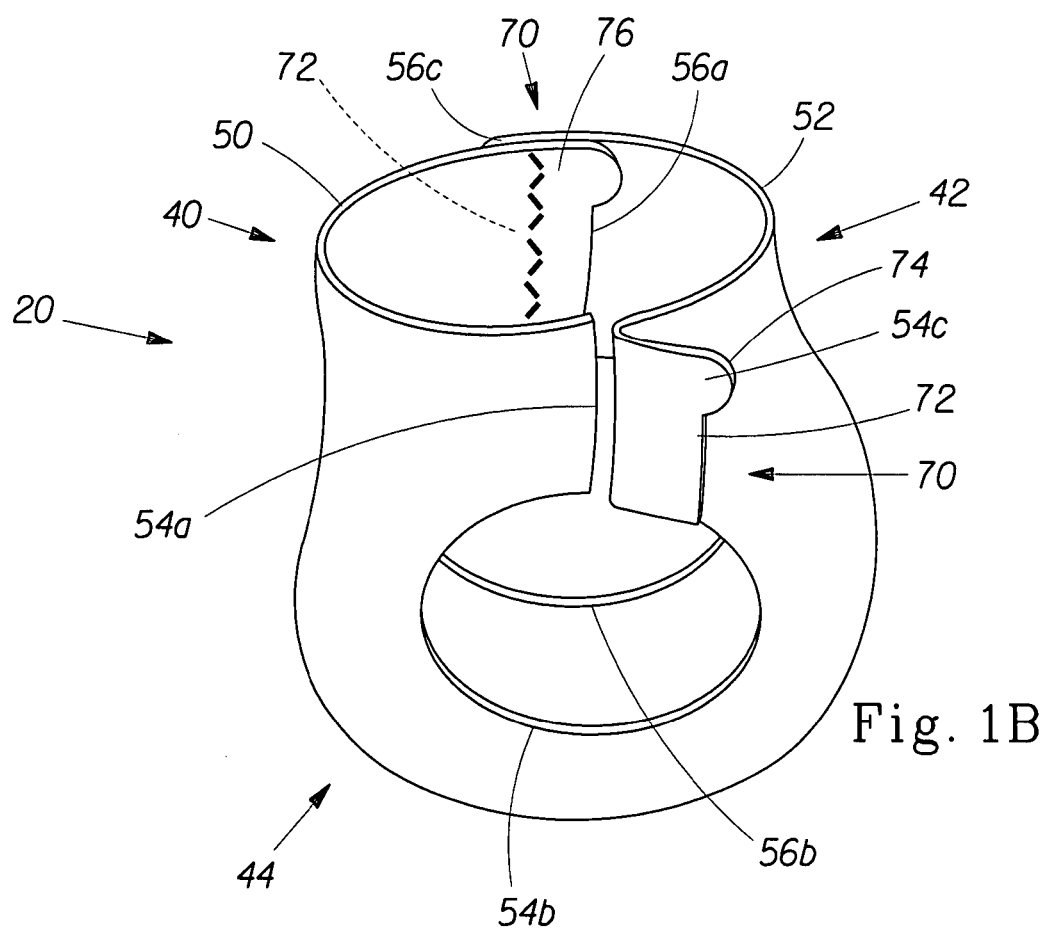
FIG. 1B is an isometric view showing the absorbent article of FIG. 1A partially fastened.

The absorbent article 20 may be provided with an easy open feature such as shown in FIG. 1B. Such an easy open feature can comprise a single element or a combination of elements designed to make the seams of the article easier to open so as to remove the article. For example the easy open feature could comprise a gripping tab 74. Additionally an easy open bond line pattern 76 could be provided either alone or in combination with the gripping tab 74. The easy open bond line pattern 76 shown in FIG. 1B can act as a type of "zipper" structure allowing propagation of an opening force along the side of the article 20. In some embodiments, the easy open bond line pattern may comprise indicia which indicate where to open the article. Such indicia are described in Co-pending application Ser. No. 11/198,614 filed on Aug. 5, 2005 on behalf of Liu et al.

Other easy open features could include a line of weakness, a notch or tab designed to propagate a tear, a tab gripping area or similar feature designed to allow for more easy release of a refastenable side fastener. Easy open features such as those described above can be provided if desired on articles having refastenable features or those which do not have refastenable fasteners—for example, a pant like garment with pre-formed side seams incorporating an easy open feature which can be used once, but which does not allow for refastenability once opened. Additionally, features which allow a child to more easily lower (or raise) the garment such as handles, printed indications of gripping features or the like such as those described in Co-pending application Ser. Nos. 11/083,606 and 11/083,607 and may also be included.

Referring back to FIG. 1A, the absorbent article 20 may further comprise a sensation member 80. As shown, in some embodiments, the sensation member 80 can be disposed on the absorbent article 20 such that the sensation member 80 forms a portion of a wearer-facing surface of the absorbent article 20. Exemplary orientations and embodiments of the sensation member 80 are discussed further hereafter.

In some embodiments, during insults of urine, at least a portion of the urine can penetrate through the sensation member 80 to the topsheet 60. The flow of urine can cause the sensation member 80 to provide a feedback response to the wearer indicating to the wearer that he or she has urinated. As stated previously, a wetness feedback response can be provided, a temperature feedback response can be provided, or a combination of a wetness and temperature feedback response can be provided.

The sensation member 80, in some embodiments can be configured to provide a wetness feedback response. For example, sensation members constructed in accordance with the present invention can be designed such that the sensation member retains urine for a temporary period of time. The retention of urine for a temporary period of time can create a wetness feedback response which is provided to the wearer.

Figure 2:
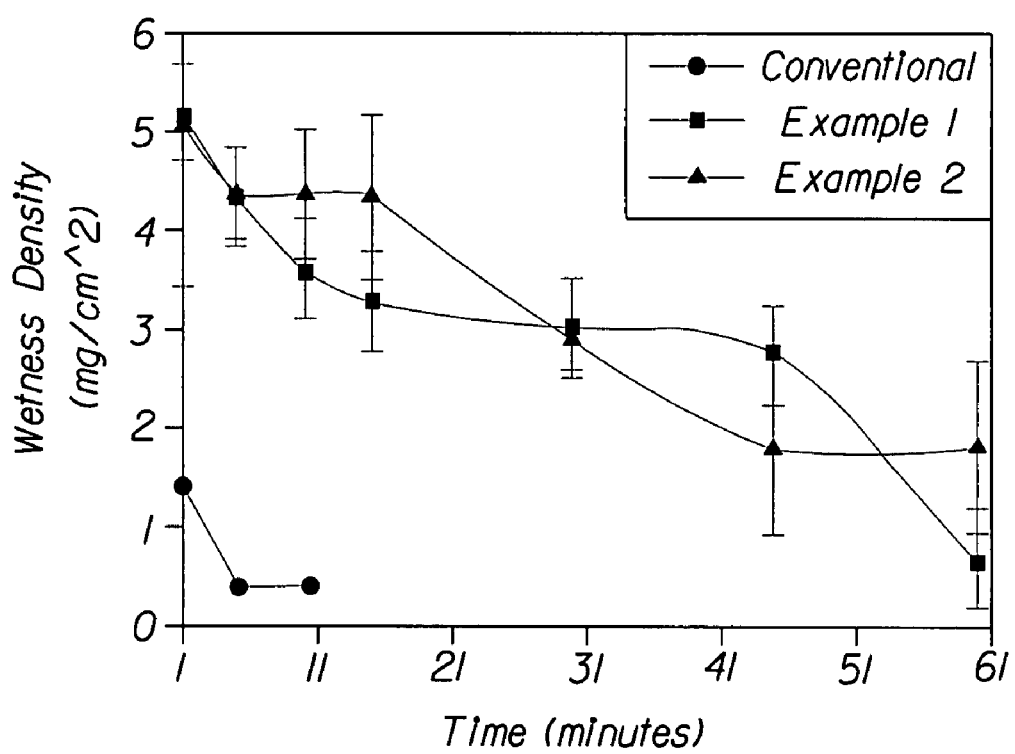
FIG. 2 is a graph showing wetness density versus time in a sensation member.

As shown in FIG. 2, a graph depicting the wetness density versus time for various materials is provided. For a wetness sensation feedback response, the amount of moisture contacting the skin should be of a sufficient quantity to be noticed by the wearer. For example, in some embodiments, a sensation member constructed in accordance with the present invention can have a Wetness Density (WD) of greater than about 2 mg/cm$^2$ at about 60 seconds or greater than about 4 mg/cm$^2$ at about 60 seconds or greater than about 5 gm/cm$^2$ at about 60 seconds. Additionally, it may be desired that the WD at about 10 minutes is less than about 80% or less than about 75% or less than about 70% of the WD measured at about 60 seconds. In some embodiments, the sensation member can have a WD of between about 1.2 mg/cm$^2$ at about 60 seconds to about 5 mg/cm$^2$ at about 60 seconds or any individual number within the range. In some embodiments, the sensation member can have a WD of between about 0.5 mg/cm$^2$ at about 10 minutes to about 4.7 mg/cm$^2$ at about 10 minutes or any individual number within the range. In some embodiments, the sensation member can have a WED of less than about 4.7 mg/cm$^2$ at about 10 minutes.

As stated previously, the feedback response provided by the sensation member should be temporary. Accordingly, the wetness density of the sensation member, as a function of time, should decrease. For example, in some embodiments, the sensation member can have a WD of less than about 3 mg/cm$^2$ at about 60 minutes. In some embodiments, the sensation member can have a WD of less than about 1 mg/cm$^2$ at about 60 minutes. In some embodiments, the sensation member can have a WD of between about 0.5 mg/cm$^2$ at about 60 minutes to about 3 mg/cm at about 60 minutes or any individual number within the range.

Additionally, where a feedback response comprising a temperature response is desired, a material can be selected where the WD at about 60 seconds is significantly less than the WD at about 30 seconds. For example, the WD at about 60 seconds, can be less than about 80%, or less than about 75%, or less than about 70%, or less than about 50% of the WD measured at about 30 seconds. Without wishing to be bound by theory, it is believed that a rapid decrease in the WD may correspond, at least in part, to evaporation of urine from the sensation member. The evaporation of urine may be utilized to create a temperature feedback response.

The above ranges, e.g. at 30 seconds, at 60 second, at 10 minutes, and at about 60 minutes can be utilized in conjunction with one another, in some embodiments. For example, a sensation member constructed in accordance with the present invention can be designed to provide both a wetness sensation and a temperature response between the time of initial insult and about 60 minutes. As stated previously, the sensation member, in some embodiments, can be designed such that between 30 seconds and 60 seconds a first rate of decrease in WD occurs thereby providing a feedback response to the wearer which is primarily a temperature response. Subsequently, after about 60 seconds, the WD may decrease at a second rate which is less than the first rate thereby providing a feedback response to the wearer which is primarily a wetness sensation. Alternatively, the change in feedback response from a primarily temperature response to a primarily a wetness sensation can occur at any suitable time.

Regarding FIG. 2, example 1 was a disposable absorbent article comprising a sensation member which was a 10 gsm SSMMS polypropylene manufactured by Avgol Ltd. of Tel-Aviv, Israel. Example 2 was a disposable absorbent article comprising a sensation member which was a Lyocell/polypropylene blend with 5-25% Lyocell/75-95% polypropylene manufactured by Albis Plastics of Rosenberg, Tex. The conventional sample measured was a Pampers® brand disposable absorbent article available under the name Feel-N-Learn® manufactured by The Procter & Gamble Company of Cincinnati, Ohio.

There are several factors which can impact the duration of the feedback response and/or the amount of time the sensation member retains liquid. For example, the capillary pressure and the absorptive capacity of the sensation member can impact the duration of the feedback response and the amount of time the sensation member retains liquid, in part.

Additionally, there are several factors which can impact the unmistakability of the wetness signal. In addition to the capillary pressure and the absorptive capacity of the sensation member, the wicking factor of the sensation member can similarly impact the unmistakability of the wetness signal.

Capillary Pressure

The capillary pressure can impact the slope of a WD curve. For example, a capillary pressure which is too high will tend to flatten out the WD curve which can equate to a retention of liquid in the sensation member for longer periods of time. The higher the capillary pressure, in general, the more resistant the sensation member is to giving up liquid. Therefore, a higher capillary pressure can equate to an increased duration of the feedback response to the wearer. Unfortunately, increased duration of the feedback response can lead to prolonged exposure of the wearer's skin to urine which in turn may lead to skin health issues.

As another example, a capillary pressure which is too low will tend to increase the negative slope of the WD curve. The increase in the negative slope of the WD curve can cause the sensation member to lose liquid too quickly to provide an adequate feedback response to the wearer.

Sensation members constructed in accordance with the present invention, in some embodiments, can have a capillary pressure of greater than about 50 mm of water. In some embodiments, the capillary pressure can be between about 50 mm of water to about 500 mm of water or any individual number within the range. In some embodiments, the capillary pressure can be between about 100 mm of water to about 250 mm of water. In some embodiments, the capillary pressure can be about 220 mm of water. In some embodiments, the capillary pressure can be greater than about 100 mm of water.

In accordance with the present invention, the capillary pressure can be achieved through careful material selection, through treatment of the material, or through a combination of both. For example, in embodiments where the sensation member comprises a nonwoven material, the pore size of the nonwoven material can impact the capillary pressure of the sensation member. For example, larger pore sizes may result in a lower capillary pressure versus smaller pore sizes. The fiber chemistry can similarly impact the capillary pressure of a material. For example, polypropylene fibers may have a lower capillary pressure than pulp fibers.

In some embodiments, the capillary pressure can be achieved by treating the sensation member with a surfactant, mechanically treating the sensation member, and/or corona treatment of the sensation member. A suitable example of mechanical treatment involves compressing the sensation member. In some embodiments, the compression of the sensation member can reduce the pore size between the fibers of the material thereby increasing the capillary pressure of the material.

Test methods for measuring the capillary pressure are discussed hereafter.

Absorptive Capacity

The absorptive capacity of a sensation member can impact the amount of liquid which the sensation member stores. For example, for the same volume of urine, a sensation member with a higher absorptive capacity will begin at a higher level on the y-axis of the WD curve of FIG. 2 than a material having a lower absorptive capacity. Similar to the capillary pressure, the absorptive capacity should neither be too high nor too low. For example, an absorptive capacity which is too high may correlate to a higher amount of liquid which is in contact with the skin of the wearer. This in turn may lead to skin health issues. As another example, an absorptive capacity which is too low may correlate to a very weak feedback response provided by the sensation member. The absorptive capacity of the sensation member is measured in accordance with EDANA 10.4-02.

Sensation members constructed in accordance with the present invention, in some embodiments, can have an absorptive capacity of greater than about 0.01 g/cm$^2$ and less than about 0.25 g/cm$^2$ or any individual number within the range. In some embodiments, the sensation member can have an absorptive capacity of about 0.14 g/cm$^2$.

Similar to the discussion of capillary pressure above, the absorptive capacity of the sensation member can be achieved through careful material selection, through treatment of the material, or through a combination of both. For example, in embodiments where the sensation member comprises a nonwoven material, the basis weight of the nonwoven material can impact the absorptive capacity of the sensation member. In general, a material having a higher basis weight has a higher absorptive capacity than the same material having a lower basis weight.

In some embodiments the absorptive capacity of the sensation member can be achieved via mechanical treatment. For example, the sensation member can be compressed thereby decreasing its volume. As another example, the sensation member may be bonded to another substrate or the fibers of the sensation member can be bonded. A material having a high bond density tends to have less absorptive capacity than does the same material having a lower bond density.

Wicking Factor

The wicking factor may impact the amount of wetted surface area in the x-y plane available for contacting the wearer's skin. For example, a first sensation member with a high wicking factor, e.g. 100 mm at one minute, allows for greater urine migration in an x-y plane of the first sensation member than a second sensation member having a wicking factor of about 10 mm at one minute. The greater the migration in the x-y plane, the more wetted surface area of the sensation member is available to contact the skin of the wearer. The wicking capability of the sensation member is measured in accordance with EDANA 10.4-02.

In some embodiments, the wicking factor can be greater than about 20 mm at about one minute. In some embodiments, the wicking factor can be in a range from about 20 mm at about one minute to about 100 mm at about one minute or any individual number within the range. In some embodiments, the wicking factor can be in a range from about 50 mm at about one minute to about 100 mm at about one minute. In some embodiments, the wicking factor can be in a range from between about 70 mm at about one minute to about 100 mm at about one minute.

In accordance with the present invention, the wicking factors can be achieved through careful material selection, through treatment of the material, or through a combination of both. For example, the wicking factor of a material can be impacted by the pore size between the fibers which make up the sensation member. In some cases, the smaller the pore size, the greater the wicking factor of the material.

In some embodiments, the wicking factor can be influenced through mechanical treatment. For example, the wicking of the sensation member, in some embodiments, can be increased by mechanically compressing or embossing channels onto the sensation member.

In some embodiments, the wicking factor of the sensation member can be influenced by chemically treating the sensation member. For example, a surfactant can be added to the sensation member to increase its wicking factor.

Exemplary Sensation Member Configurations

As stated previously, the sensation member can be chemically treated such that the wicking factor, capillary pressure, and/or the absorptive capacity can be modified as desired. For example, in some embodiments, a first substance can be applied to the sensation member on a first surface of the sensation member, and/or a second substance can be applied to a second surface of the sensation member. In some embodiments, the first surface may correspond to a top surface of the sensation member while the second surface corresponds to a bottom surface of the sensation member. In some embodiments, the first surface and/or second surface may correspond to a zone or a plurality of zones in the x-y plane of the sensation member.

For the purposes of the present invention, application of a substance to the sensation member or a surface of the sensation member can be via coating, spraying, impregnating, the like, or any combinations thereof. Additionally, embodiments are contemplated where the treatments comprise separate layers which are included in the sensation member.

The feedback response generated by the sensation member should contact the wearer's skin to elicit a sensation. In some embodiments, the article and sensation member can be designed to enable at least intermittent, contact, over time, between the sensation member and the wearer's skin. In some embodiments, the article and the sensation member can be designed to enable continuous contact, over time, between the wearer facing surface of the sensation member and the wearer's skin in all body positions and during all activities in which the wearer may engage. It may be desired that the area of contact on the wearer's body comprises an area having a relatively higher concentration of nerve endings. In the region of the body commonly covered by disposable absorbent articles such as pant-like diapers or training pants, the genital, perineal, perianal, inner thigh, and lower abdomen have a relatively higher nerve concentration and can be preferred contact areas.

An example of a suitable method of promoting contact between the sensation member and the wearer can be to provide a raised sensation member as described herein. In these embodiments, the skin contact can be effected by providing a sensation member at least locally detached from underlaying layers in at least the desired region of contact and elastically foreshortening the sensation member, or a structure to which the sensation member is affixed, causing the sensation member to be lifted in the z-direction toward the body. Additionally, in certain embodiments, the elastic lifting members may cause the sensation member to contact the body with sufficient force and resiliency to allow the sensation member to continue to contact the body during wearer motion, or to quickly re-establish contact in the event that contact is temporarily broken.

Another example of a method of promoting skin contact may also be employed in place of, or in addition to the method described hereinabove. For example, at least a portion of the skin contacting surface of the sensation member may comprise a contact promoting substance that adheres gently to the wearer's skin and resists casual disengagement. Exemplary contact promoting substances may include skin care compositions, examples of which are disclosed in U.S. Pat. Nos. 5,607,760; 5,609,587; 5,635,191; 5,643,588; 5,968,025; 6,107,537; 6,118,041; 6,153,209; 6,716,441; and PCT Publication No. WO 95/24173; sticky lotions, examples of which are disclosed in WO 2004/087092; and adhesives, examples of which include body adhesives. In certain embodiments a water-activatable adhesive may be desirable as it would only promote contact once the wearer urinates. Water activatable adhesives for use in disposable absorbent articles are disclosed in U.S. Pat. No. 6,623,465. The skin contact promoting substance may be disposed on at least a portion of the sensation member or in a region of the topsheet or other supporting structure in proximity to the sensation member.

Additionally, skin contact may also be promoted via resilient 3-dimensional structures comprising foams or core materials. These structures may serve to hold the sensation member in contact with the wearer even during wearer motion due to their 3-dimensional resilient nature. In some embodiments, these structures may be relatively thin and unobtrusive when in a dry state and may be triggered to grow in the z-direction by contact with urine. For example, the structure may comprise a compressed foam encapsulated in a water or pH sensitive material wherein the foam is allowed to expand upon contact with urine. As another example, the structure may comprise a composition capable of evolving gas held within a semi-permeable membrane such that it inflates upon contact with urine. Further examples of structures that increase in thickness upon contact with urine include those described in U.S. Pat. Nos. 3,881,491; 3,921,232; 5,330,459; 6,186,991; and 5,797,892.

Figure 3A:
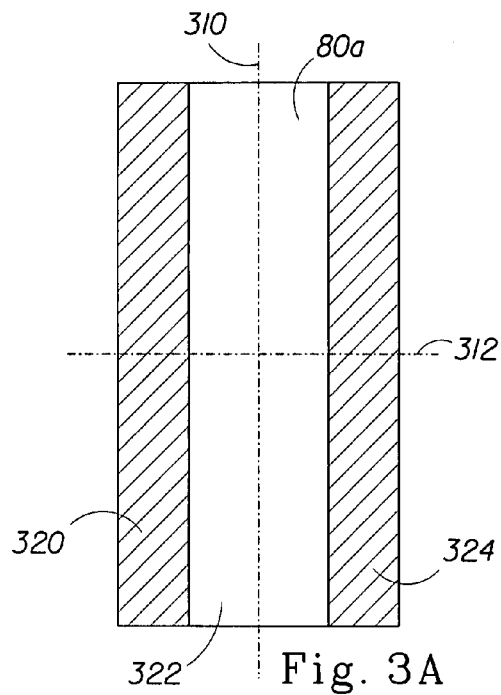
FIGS. 3A and 3B are plan views showing other embodiments of the sensation member of FIG. 1A.
Figure 3B:
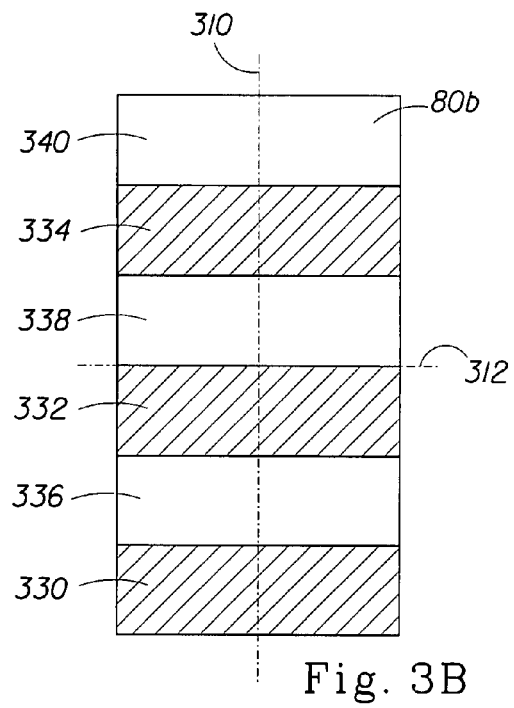

As shown in FIGS. 3A and 3B, in some embodiments, a sensation member of the present invention can be chemically treated, mechanically treated, or a combination thereof at preselected areas. As shown in FIG. 3A, in some embodiments, the sensation member 80A may comprise zones of treatment 320 and 324. As shown, in some embodiments, the zones of treatment may extend generally parallel to a longitudinal axis 310 of the sensation member 80A. Additionally, in some embodiments, the zones of treatment 320 and 324 can be separated by a non-treated zone 322.

As shown in FIG. 3B, a sensation member 80B may comprise zones of treatment 330, 332, and 334, which extend generally parallel to a lateral axis 312 of the sensation member 80B. The zones of treatment 330, 332, and 334, can be spaced apart by non-treated zones 336, 338, and 340.

Regarding FIGS. 3A and 3B, embodiments are contemplated where at least one of the zones of treatment is mechanically treated and/or chemically treated. Additionally, embodiments are contemplated where a sensation member comprises a plurality of zones of treatment at least one of which comprises chemically treated zone of treatment and a mechanically treated zone of treatment.

The zones of treatment described with regard to FIGS. 3A and 3B are merely examples of contemplated embodiments. The zones may be of any suitable number, shape, size, and in any suitable orientation. Additionally, embodiments are contemplated where the sensation members are treated for gender specificity. For example, a sensation member in a disposable article for a boy may be treated or non-treated in location which is nearer to a front waist edge than a sensation member in a disposable article for a girl.

In some embodiments, the non-treated zones, e.g. 322, 336, 338, 340 (shown in FIGS. 3A and 3B), may comprise separate layers from those of the zones of treatment. For example, as shown in FIG. 3A, the zones of treatment 320 and 324 may comprise separate layers which are each joined to the non-treated zone 322 which is also a separate layer. The zones of treatment and non-treated zones of FIG. 3B can be configured similarly to those of FIG. 3A.

Examples of suitable chemical treatments include adding hydrophilic substances, hydrophobic substances, and/or temperature sensation agents. Any suitable hydrophilic substance can be used. Some suitable examples of hydrophilic coatings include surfactants, such as the NUWET silicone surfactant available from GE Silicones of Wilton, Conn.

Any suitable temperature sensation agent can be utilized in conjunction with the present invention. For example, in some embodiments, a sensation member may also comprise an active component in the form of a temperature sensation agent (composition or structure). In some embodiments, the temperature sensation agent may be utilized in place of the hydrophilic substance, in conjunction with the hydrophilic substance, or combined (e.g., mixed) with the hydrophilic substance.

In some embodiments, where the sensation member comprises a temperature sensation agent, the feedback response provided to the wearer can be a temperature response. In some embodiments, where the sensation member comprises a temperature sensation agent, the feedback response provided to the wearer can be a perceived temperature change by the wearer. Examples of both are provided hereafter.

Some examples of suitable temperature sensation agents may include those materials that produce a temperature change (i.e., involve an endothermic or an exothermic reaction), as well as those that produce the sensation that a temperature change has occurred without actually producing a temperature change. For example, the temperature sensation agent may be a cooling agent. A suitable example of a cooling agent is AQUACOOL dye manufactured by United Polymer Technology of Akron, Ohio. The AQUACOOL dye is a water-soluble dye that changes temperatures when brought into contact with water. Another example of cooling agent may be menthol or a menthol derivative, which chemicals are believed to provide the sensation of a temperature change, while not actually producing a temperature change. The COOLACT P and COOLACT 10 products manufactured by LIPO Chemicals of Paterson, N.J. are examples of menthol derivative products which may be suitable. Other examples of temperature change agents (e.g., endothermic salts) that may be suitable temperature sensation agents may be found in U.S. Pat. No. 6,642,427.

Any suitable hydrophobic substance may be used. Additionally, the hydrophobic agent may include a diverse range of materials, including lotions, creams etc. Some examples of suitable hydrophobic substances include hydrophobic coatings (HFC) and liquid-impermeable surface coatings (LISC). In particular, the hydrophobic substance may be made in accordance with the disclosure of U.S. Published Application No. 2005/0177123. Alternatively, the substance may be acrylic polymer (e.g., acrylamide, ethyl alcohol, n-butyl alcohol, methyl-methacrylate, acrylamide, acrylonitrile, or combinations thereof) emulsions manufactured and sold, for example, under the ROHATOL tradename by Lanxess Corp. of Pittsburg, Pa., the RH-MW1845K tradename by Rohm & Haas of Philadelphia, Pa., or the FA1, FA2, or FA3 tradenames by PolymerLatex International GmbH of Marl, Germany. Additionally, in some embodiments, the hydrophilic substance and/or temperature sensation agent may or may not be included (the temperature sensation agent being combinable with either the hydrophilic or hydrophobic agent, if present).

Additionally, it will be also recognized that the hydrophilic substance, hydrophobic substance, and/or temperature sensation agent may include a diverse range of materials, including lotions, creams and the like. Some suitable examples of lotions are described in U.S. Pat. Nos. 5,607,760; 5,609,587; 5,635,191; 5,643,588; 5,968,025; 6,107,537; 6,118,041; 6,153,209; 6,716,441; and PCT Publication No. WO 95/24173.

Examples of suitable mechanical treatments may include compression, bonding, compression bonding, fusion bonding, calendering, necking, heated compression bonding, or the like. Any suitable mechanical treatment may be utilized. Other suitable mechanical processes may include mechanical activation, SELFing, tentering, and aperturing.

The sensation member of the present invention can be disposed within an absorbent article in many different configurations. Some examples of suitable configurations include those described in U.S. Pat. Nos. 6,627,786; 4,022,210; 5,342,343; 5,649,914; 5,658,268; 5,702,376; 5,797,892; 6,727,404; 6,229,063; 6,320,096; 6,169,225; 6,146,367; 5,885,264; 6,726,668; 5,891,124; 6,958,432; U.S. Patent Application Publication Nos. 2005/0096612; 2003/0114807; 2003/0114821; 2003/0125682; 2004/0220540; and 2005/0049568. Other examples of suitable configurations are provided below.

Figure 4:
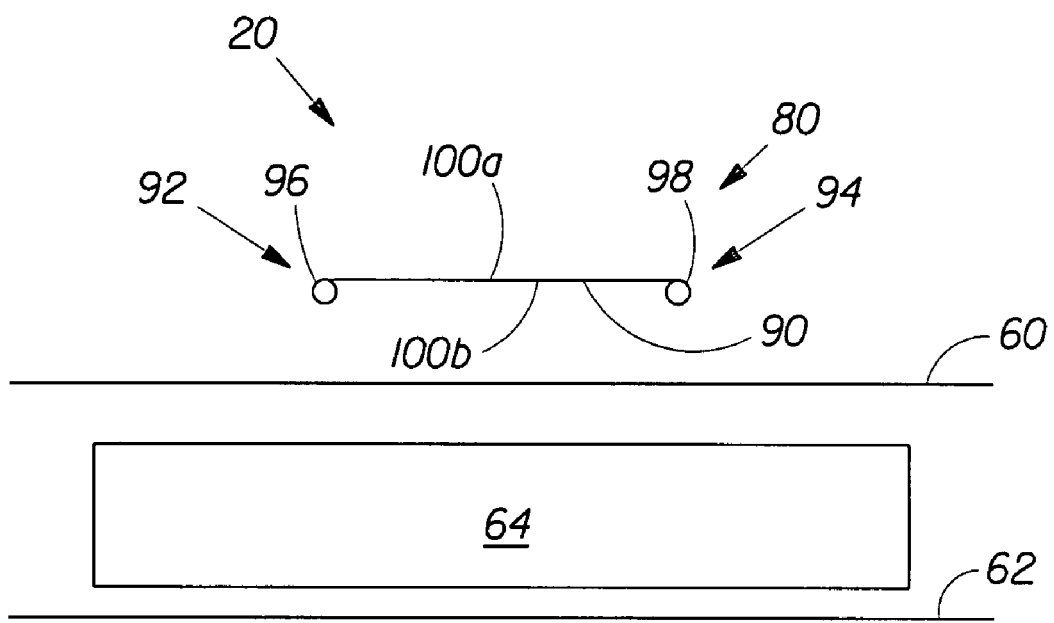
FIG. 4 is a cross section showing the absorbent article of FIG. 1A through line 4-4.

As another example, as shown in FIG. 4, in some embodiments, the sensation member 80 may comprise a first substrate 90. In some embodiments, the first substrate 90 has first and second sides 92, 94 that may be parallel to the longitudinal axis 30 (shown in FIG. 1) of the article 20. For example, a first elastic member 96 may be attached to the first substrate 90 at the first side 92, while a second 98 elastic member may be attached to the first substrate 90 at the second side 94. The elastic members 96, 98 may extend along the entire length of the first substrate 90, or only a portion thereof. A fully or partially elasticized first substrate 90 may to tend to draw the sensation member 80 toward or against the skin of the wearer. Alternatively, the first substrate 90 may be formed to have a lesser length than another layer disposed relatively exteriorly, etc.

The first substrate 90 comprises a first surface 100A and a second surface 100B. In some embodiments, the sensation member 80 may further comprise a treatment. For example, treatments can be applied to the first surface 100A and/or second surface 100B. Any suitable treatment may be applied to the first surface 100A and/or second surface 100B. For example, in some embodiments, a hydrophilic substance can be applied to the first surface 100A and/or a hydrophobic substance can be applied to the second surface 100B. As another example, in some embodiments, a temperature sensation agent can be applied to the first surface 100A and/or second surface 100B in conjunction with the hydrophilic substance, hydrophobic substance, or independently of any other treatment.

The spacing of the first and second sides 92, 94 of the first substrate 90 and the width of the application of the substance, e.g. hydrophilic, hydrophobic, and/or temperature agent, if present, may be determined to allow enough liquid to bypass the sensation member 80 to the core 64 so as to prevent flooding. Flooding may result in leakage of the article 20 during urination, which is undesirable in the article 20 when it is a diaper or training pant, for example.

As shown, in some embodiments, the sensation member 80 can be disposed supedjacent to the topsheet 60 of the disposable article 20. For example, in some embodiments, the sensation member 80 can be a structure that is formed separately from, but discretely attached to, the topsheet 60.

Figure 5A:
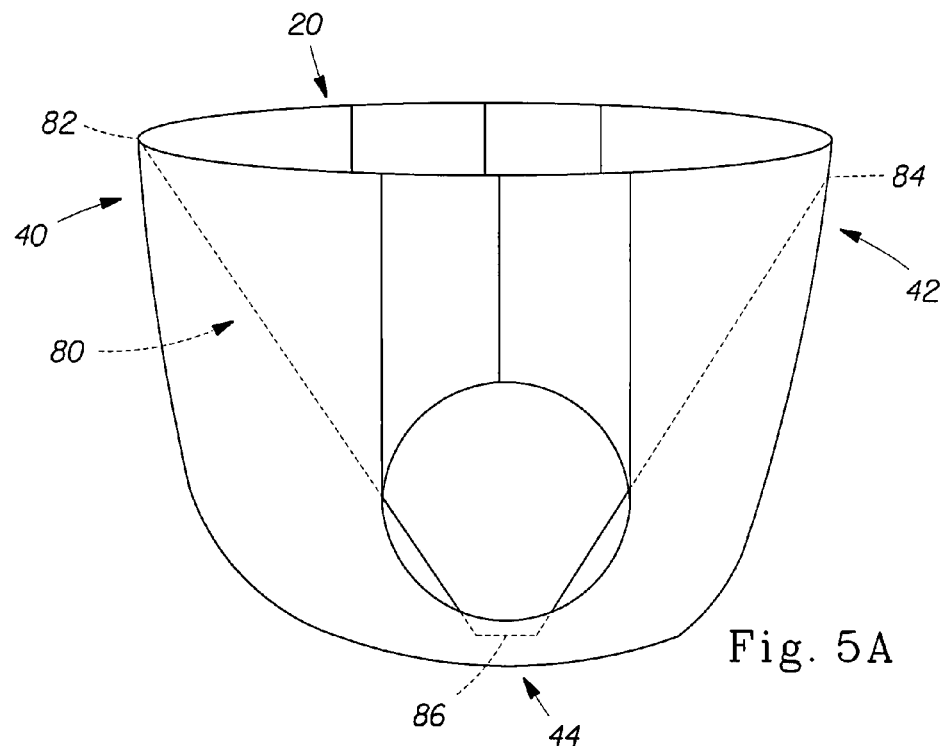
FIG. 5A is an isometric view showing the article shown in FIG. 3A illustrating a first exemplary attachment of the sensation member.

As shown in FIG. 5A, for example, the sensation member 80 can have a first laterally extending joining region or end 82 attached to the first waist region 40, and a second longitudinally opposing and laterally extending joining region or end 84 attached to the second waist region 42. In addition, the sensation member 80 may have a center joining region 86 that may be attached to the crotch region 44. It is believed that the attachment of the member 80 to the crotch region 44 may assist in stabilizing the member 80, in facilitating fitting of the article 20 to the wearer, in preventing interference with bowel movements and in ensuring good contact with the wearer's skin.

Figure 5B:
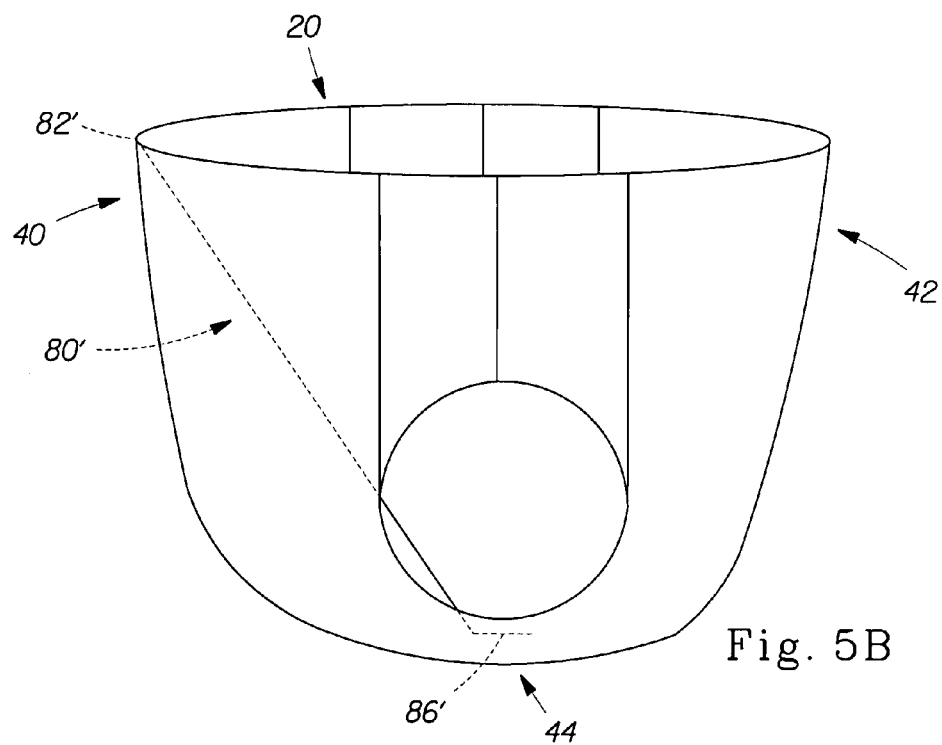
FIG. 5B is an isometric view showing the article shown in FIG. 3A illustrating a second exemplary attachment of the sensation member.

As shown in FIG. 5B, in some embodiments, the sensation member 80 may comprise the first laterally extending joining region or end 82 attached to the first waist region 40 and the center joining region 86 that may be attached to the crotch region 44. In some embodiments, the sensation member 80 may comprise the second laterally extending joining region 84 (shown in FIG. 5A) and the center joining region 86 attached to the crotch region.

Regarding FIG. 1A, the disposable absorbent article 20, in some embodiments, may have visible highlighting 110. As shown, in some embodiments, the visible highlighting 110 may comprise a pattern of wavy lines and circles in the interior of the article associated with the sensation member or members 80 to indicate the presence of the sensation member or members 80 and thereby facilitate an opportunity for the urinary toilet training of the wearer of the article. Such visible highlighting is described in U.S. Published Application No. 2005/0096612. Although a sensation member lacking this visible highlighting is fully functional in terms of providing a noticeable wetness and/or temperature signal to the wearer, the caregiver might overlook or forget the possibility of capitalizing on each opportunity for urinary toilet training if the body-facing portion of the absorbent article presents a generally uniform appearance, such as in absorbent articles that present a generally uniform white appearance on their body-facing surfaces.

In some embodiments, the visible highlighting may be provided by impressing or embossing the sensation member or one of it layers. The impressed, embossed, or bonded portions of the sensation member may provide a tactile sensation in addition to visibly highlighting the presence and location of the sensation member. For example, a raised area or a recessed area or the combination of raised and recessed areas adjacent to each other may be felt by the hand and, in some embodiments, may be felt by the wearer while wearing the article. Further examples of visible highlighting, graphics, etc. are discussed in U.S. Patent Publication No. 2005/0129743A1; U.S. Patent Publication No. 2005/0125923A1; U.S. Patent Publication No. 2005/0125877A1; U.S. Pat. Nos. 4,089,765; 5,989,380; 6,548,431; WO 2004/071780; U.S. Patent Publication No. 2005/0129743A1; U.S. Patent Publication No. 2005/0125923A1; U.S. Patent Publication No. 2005/0125877A1; U.S. patent application Ser. No. 11/098,362, filed in the name of Roe et al. on Apr. 4, 2005; and U.S. patent application Ser. No. 11/351,745, filed in the name of Roe et al. on Feb. 10, 2006.

Figure 6A:
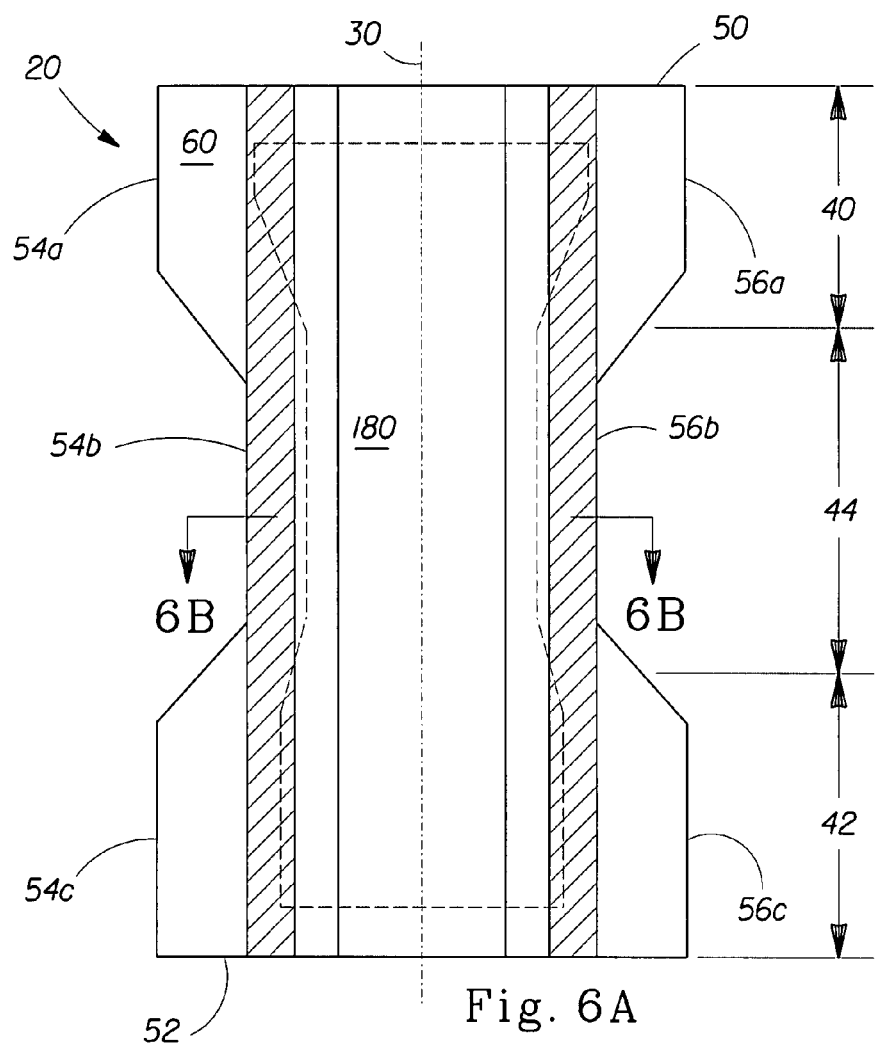
FIG. 6A is a plan view of an absorbent article having a sensation member according to another embodiment of the present disclosure.
Figure 6B:
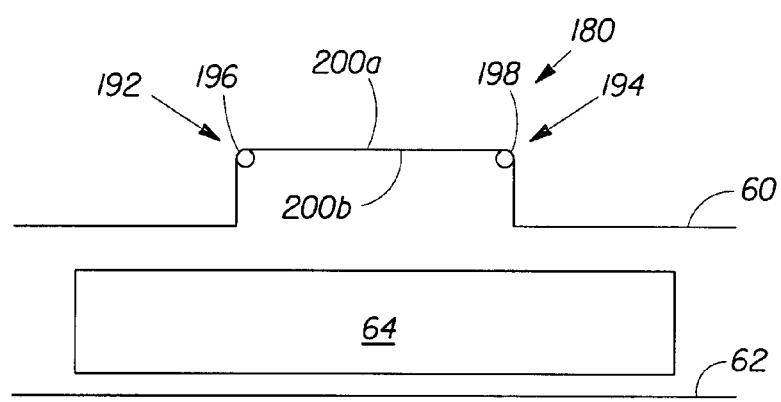
FIG. 6B is a cross-sectional view showing the article of FIG. 5A.

Other suitable exemplary configurations for a sensation member constructed in accordance with the present invention include, the embodiments described with regard to FIGS. 6A and 6B. As shown in FIG. 6A and 6B, in some embodiments, a sensation member 180 may comprise a portion of the topsheet 60 of the disposable article 20 space from the core 64. As shown, in some embodiments, a section of the topsheet 60 can be folded to define the sensation member 180. For example, as shown, the topsheet 60 can be folded along the sides 192, 194 thereby forming a portion of the sensation member 180. The elastic members 196, 198 can then be disposed beneath the topsheet 60 in the space between the topsheet 60 and the core 64. In this fashion, the sensation member 180 may be integrated to a greater degree to the remainder of the article 20 than the sensation member 80 (shown in FIG. 4), thereby reducing the likelihood that the sensation member 180 will become detached from the remainder of the article 20.

As shown, the sensation member 180 may comprise first and second sides 192, 194 that are generally parallel to the longitudinal axis 30 of the article 20. Elastic members 196, 198 may be attached to the sensation member 180 at the sides 192, 194 so as to elasticize the sensation member 180, which may assist in bringing the sensation member 180 in to close contact with the skin of the wearer. Similar to the sensation member 80, the sensation member 180 may comprise a hydrophilic substance, a hydrophobic substance, and/or a thermal sensation agent applied to a first surface 200A and/or a second surface 200B. Each can be applied to the sensation member 180 as described heretofore with regard to their application to the sensation member 80. Additionally, the sensation member 180 may comprise visible highlighting as described with regard to the sensation member 80.

Figure 7A:
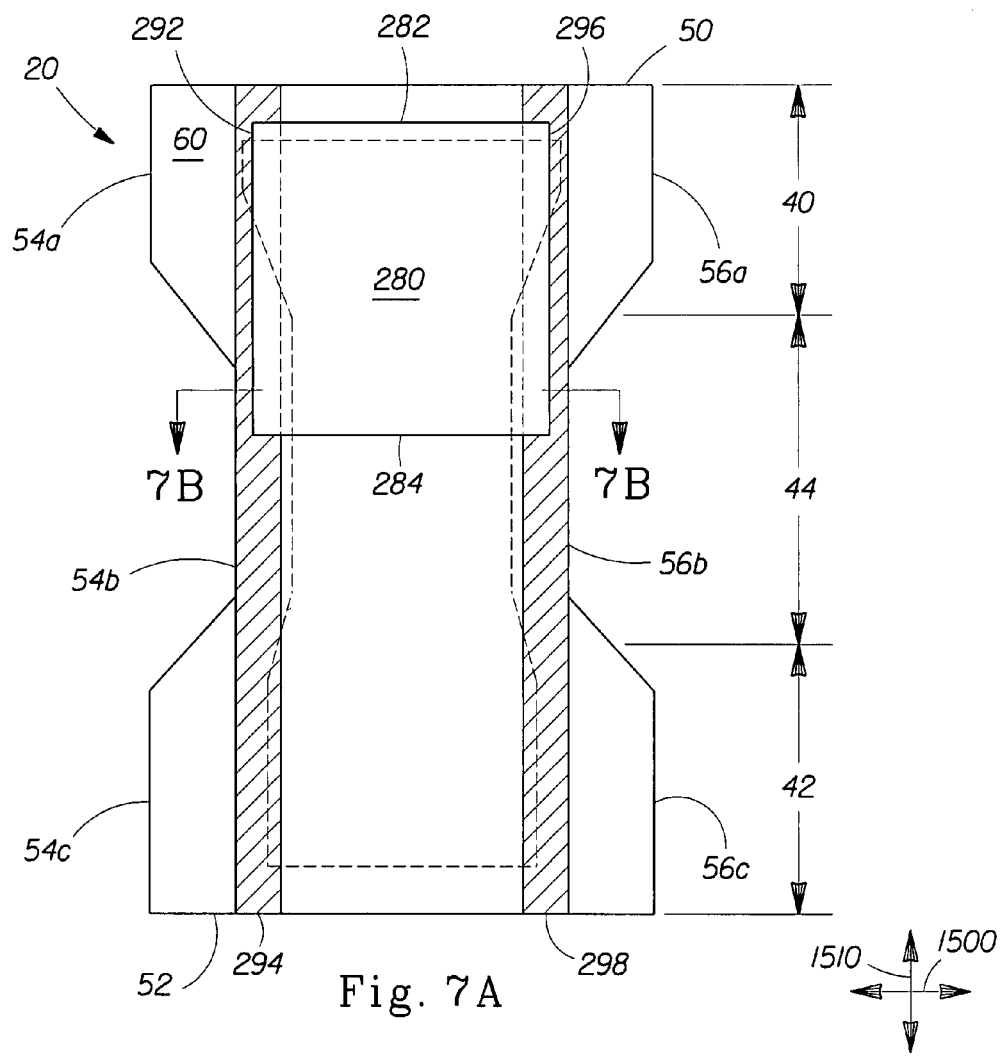
FIG. 7A is a plan view showing an absorbent article having a sensation member according to a further embodiment of the present disclosure.

As shown in FIG. 7A, a sensation member 280 is shown with the barrier leg cuffs folded back slightly to expose the sensation member 280. In some embodiments, the sensation member 280 may comprise a first laterally extending end 282 and a second longitudinally opposing and laterally extending end 284. The lateral direction and the longitudinal direction are denoted by arrows 1500 and 1510, respectively. In some embodiments, the distance between the ends 282, 284 can be shorter than the distance between the ends 50, 52, and/or even the distance between end 50 and the crotch region 44. In some embodiments, the position of the ends 282, 284 relative to the ends 50, 52 and the spacing between the ends 282, 284 can be such that the likelihood that the sensation member 280 will be wetted with urine is enhanced.

Figure 7B:
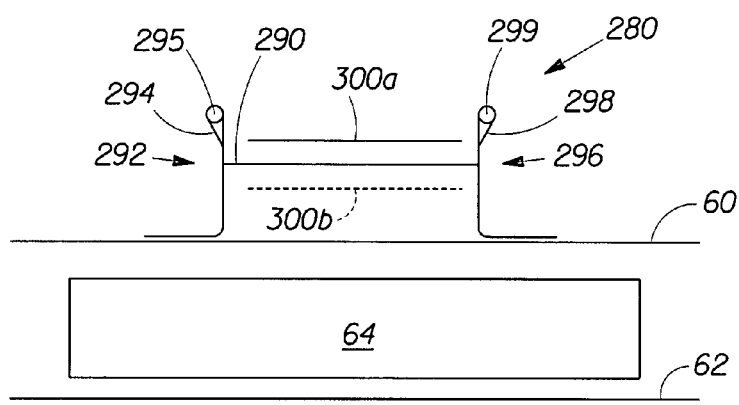
FIG. 7B is a cross-sectional view of the article of FIG. 6A.

As shown in FIG. 7B, in some embodiments, the sensation member 280 may comprise a sensation layer 290. The layer 290 can extend between the ends 282, 284. As shown, in some embodiments, a first longitudinal edge 292 of the sensation layer 290 can be attached to a first barrier leg cuff 294 which can be attached to the topsheet 60, while a laterally opposed, longitudinal edge 296 can be attached to a second, spaced barrier leg cuff 298, which can also be attached to the topsheet 60. Each barrier leg cuff 294, 298 may comprise an elastic member 295, 299. In this fashion, it is not necessary to attach separate elastic members to the sensation layer 290, but the elastic members 295, 299 of the barrier leg cuffs 294, 298 instead may urge the sensation member 280 into contact with the skin of the wearer.

It is believed that the attachment of the sensation member 280 to the barrier leg cuffs 294, 298 may permit greater control over the spacing of the sensation member 280 relative to the topsheet 60 (i.e., distance between member 280 and topsheet 60) than had heretofore been possible. That is, by attaching the sensation member 280 along its sides 292, 296, rather than at its ends 282, 284, the spacing of the member 280 relative to the topsheet 60 may be better controlled than in those embodiments wherein the member is attached at its ends, or potentially even in those embodiments where the member is integrated into the topsheet 60 and elastic members disposed internal to the topsheet 60 are used to define, at least in part, the sensation member. Additionally, by attaching the sensation member 280 to the leg cuffs 294, 298, the dimension of the sensation member 280 perpendicular to the longitudinal axis may be greater than, for example, the sensation members 80, 180 discussed above.

The sensation layer 290 may configured in a similar manner to the sensation layer 90 discussed heretofore. For example, the sensation layer 290 comprises a first surface 300A and a second surface 300B which can be treated as described heretofore. In addition to the coatings, the sensation member 280 may further comprise visible highlighting as described heretofore with regard to the sensation member 80.

Figure 8C:
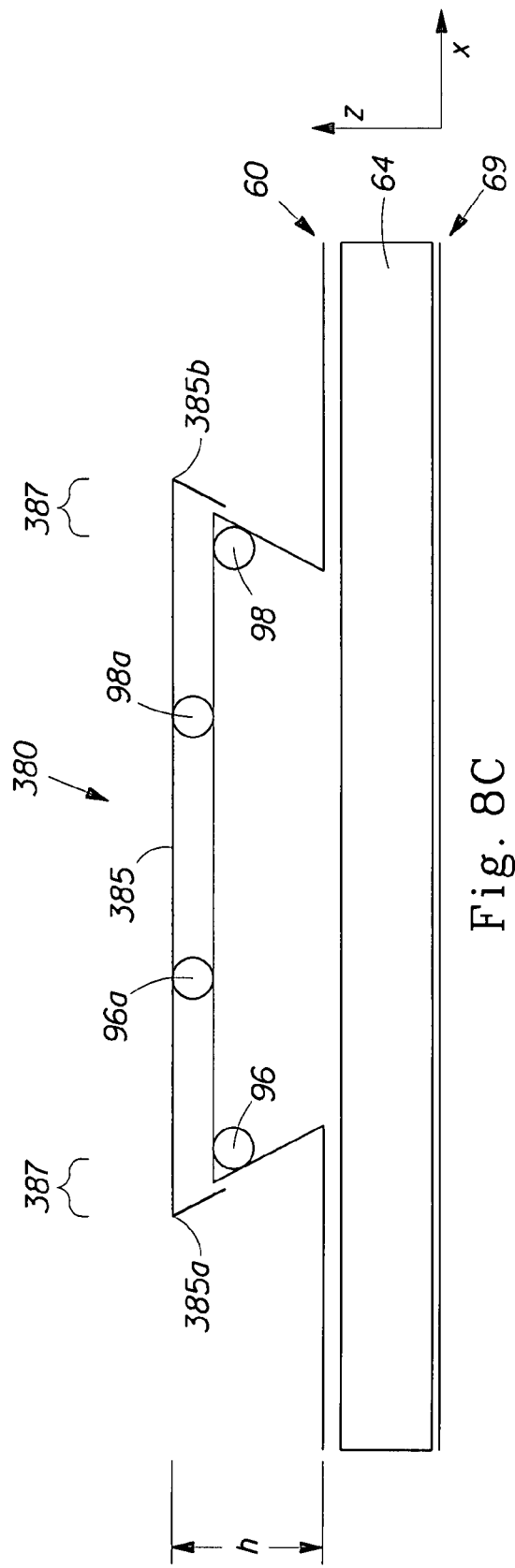

In additional embodiments shown in FIGS. 8A-8C, the sensation member 380 or any layer including the sensation member can be disposed in two parallel Z-folds 387 formed along the longitudinal length of the absorbent article. The Z-folded sensation member 380 or any layer including the sensation member may be attached to the underlying layers along the longitudinal edges of the topsheet 60 allowing the portion between the Z-folds of the topsheet 60 to float freely. Elastic elements 396, 397 may be disposed along the central region of the sensation member 380 in order to deflect the central region outward away from the absorbent core 64. Elastic elements 396, 397 may be disposed between layers of the topsheet 60, between layers of the sensation member 380, between the topsheet 60 and sensation member 380, or any other configuration that connects the elastic elements 396, 397 to the topsheet 60 and/or sensation member 380. The central region 385 may have a first side edge 385a and a second side edge 385b such that at least one of said side edges 385a, 385b has a projected height h measured the z direction between the side edge and the base of the sensation member that connects the sensation member to the absorbent article.

A disposable absorbent article including a sensation member is attached to the inner surface of a curved plate (i.e. the concave surface relative to the hypothetical center of the circle having the same curvature as the plate) having a radius of curvature of about 250 mm. The disposable absorbent article is attached to the plate such that its garment facing surface (i.e. outer cover) is in contact with the plate. In this configuration, the elastic member(s) that are disposed longitudinally on the disposable absorbent article are in an elongated configuration and are applying a force that is pulling any layer attached to the elastic member away from the core. A ruler having one end contacting the base of the sensation member and the other end pointing toward the center of the hypothetical circle formed by the curved plate, may be used to measure the distance between the base of the sensation and the side edge of the sensation member.

The Z-folded sensation member 380 allows the central region 385 to be suspended away from the core 64 and the topsheet 60. The combination of the Z-folded sensation member 380 and the elastic elements 396, 397 maintains the sensation members in proximity to the wearer's skin in the event that the diaper sags or fits loosely around the wearer.

Alternatively, additional elastic elements 396a, 397a may be disposed along the central region of the Z-folded sensation member. Elastic elements 396a, 397a, may be disposed between layers of topsheet 60, between layers of the sensation member 380, between the topsheet 60 and sensation member 380, or any other configuration that connects the elastic elements 396a, 397a to the topsheet 60 and/or sensation member 380. Elastic elements 396a, 397a provide additional support to prevent sagging and promote contact with the wearer's skin.

The absorbent article may also include a first barrier leg cuff 394 and a second barrier leg cuff 398, which may include elastic members 395, 399 respectively. First and second barrier leg cuffs are disposed on the absorbent article such that the Z-folded sensation member 380 is located between the barrier leg cuffs 395, 399. At least one of the first barrier leg cuff 394 and a second barrier leg cuff 398 has a projected height H measured the z direction between an upper edge of the barrier leg cuff and the base of the barrier leg cuff that connects the barrier leg cuff to the absorbent article.

The projected height h and H may be measured according the following method.

A disposable absorbent article including a sensation member is attached to the inner surface of a curved plate (i.e. the concave surface relative to the hypothetical center of the circle having the same curvature as the plate) having a radius of curvature of about 250 mm. The disposable absorbent article is attached to the plate such that its garment facing surface (i.e. outer cover) is in contact with the plate. In this configuration, the elastic member(s) that are disposed longitudinally on the disposable absorbent article are in an elongated configuration and are applying a force that is pulling any layer attached to the elastic member away from the core. A ruler having one end contacting the base of the sensation member and the other end pointing toward the center of the hypothetical circle formed by the curved plate, may be used to measure the distance between the base of the sensation and the side edge of the sensation member. The side edge of the sensation member is gently extended to its maximum height (i.e. without applying a force that would cause the sensation member to be torn or destroyed) and then record the measurement. The projected height measurement can be repeated at various points along the sensation member in order to determine its maximum projected height. The ruler may be moved such that one end is in contact with the base of an outer leg cuff and its other end is pointing towards the center of the hypothetical circle passing through the curved plate. The projected height H may be determined by measuring distance between the base of the outer leg cuff and the upper edge of the outer leg cuff. The upper edge of the outer leg cuff is gently extended to its maximum height (i.e. without applying a force that would cause the outer leg cuff to be torn or destroyed) and then record the measurement. The projected height measurement can be repeated at various points along the outer leg cuff in order to determine its maximum projected height.

In one embodiment, the projected height h of at least one of the first side edge 385a and a second side edge 385b is between 90% and 300%, preferably between 100% and 250%, more preferably between 100% and 200% of the projected height H of at least one of the first barrier leg cuff 394 and a second barrier leg cuff 398.

In one embodiment, the projected height h of at least one of the first side edge 385a and a second side edge 385b is between 15 mm and 50 mm, preferably between 20 mm and 45 mm, more preferably between 25 mm and 40 mm.

Figure 9:
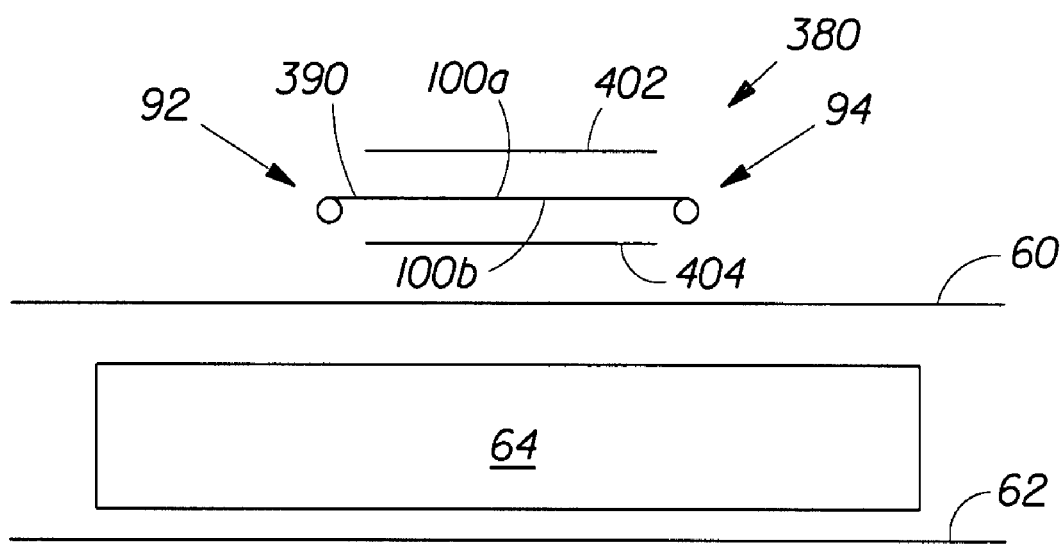
FIG. 9 is a cross-sectional view showing another embodiment of a disposable absorbent article constructed in accordance with the present invention.

As shown in FIG. 9, in some embodiments, a sensation member 380, constructed in accordance with the present invention, may comprise a laminated structure. For example, as shown, the sensation member 380 may comprise a first substrate layer 390 and adjacent layers 402 and 404. The adjacent layers 402 and/or 404 may comprise treatments as discussed herein. Alternatively, in some embodiments, the sensation member may comprise a portion of the topsheet 60 and adjacent layers as described with regard to FIG. 9.

Figure 10:
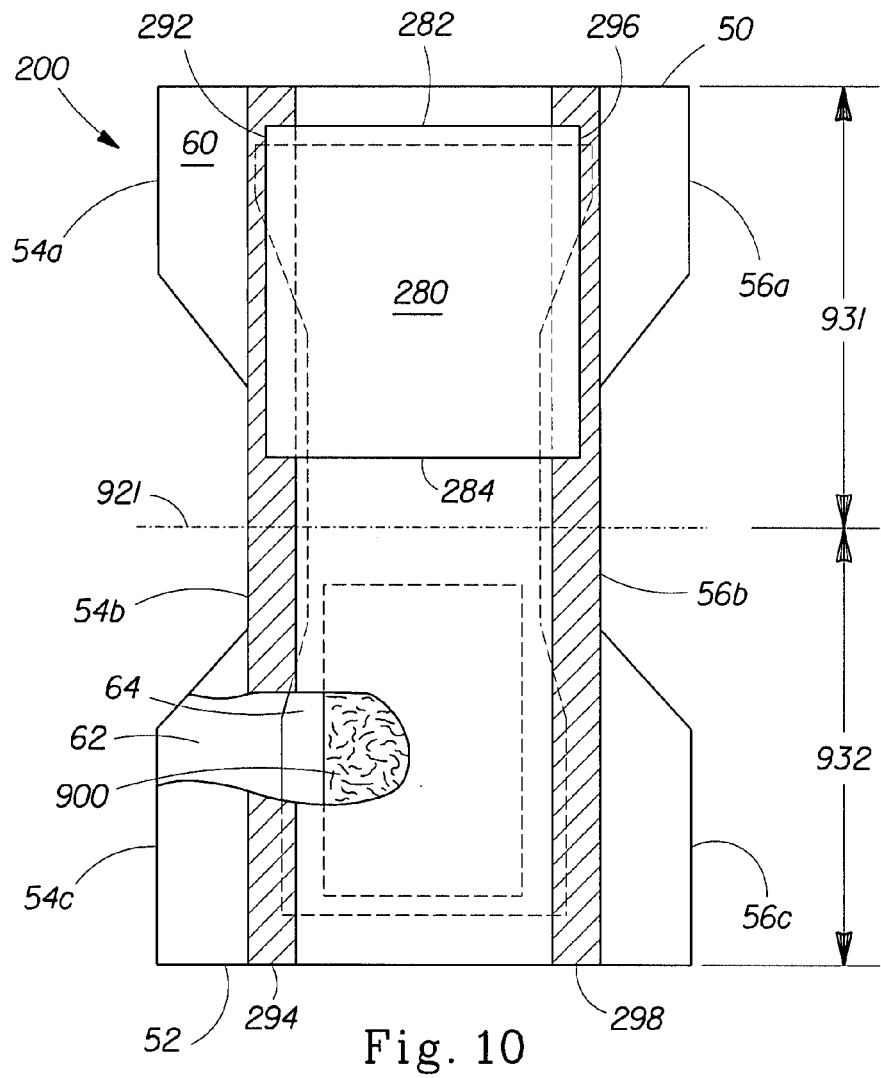
FIG. 10 is a plan view with a partial cut-away showing another embodiment of a disposable absorbent article constructed in accordance with the present invention.

As shown in FIG. 10, other embodiments are contemplated. For example a disposable absorbent article 200 constructed in accordance with the present invention may comprise a sensation member as described above with regard to FIG. 9. However, in some embodiments, the disposable absorbent article 200, in some embodiments, may further comprise a fecal management member 900. As shown, in some embodiments, the fecal management member 900 may be disposed between the topsheet 60 and the absorbent core 64.

The disposable absorbent article 200 may comprise a first region 931 and a second region 932. In some embodiments, the second region 32 of the diaper 20 can be designed to be superior in the handling of low-viscosity fecal material as compared to the first region 931. The trans-topsheet capacity reflects the diapers ability to handle low-viscosity fecal material. The second region 932 of the diaper 200, the region designed to handle low viscosity fecal material, should have a relatively high trans-topsheet capacity. Preferably, the second region 932 of the diaper 200 should have a relatively higher trans-topsheet capacity than the first region 931. The trans-topsheet capacity of the second region 932 and suitable materials for use as the fecal management member are described in U.S. Pat. Nos. 5,342,338 and 6,676,646.

As stated previously, the sensation member of the present invention can provide a feedback response which comprises a wetness sensation, a temperature response sensation, or a combination thereof. For example, a portion of the liquid absorbed by the sensation member can partially evaporate thereby causing a cooling sensation for the wearer. The evaporation of liquid can be enhanced where the backsheet of the absorbent article includes a substantially vapor permeable material. For example, in some embodiments, the backsheet can be constructed to be permeable to at least water vapor and can have a moisture vapor transmission rate (MVTR) of at least 1000 g/m$^2$/24 hr., preferably at least 1500 g/m$^2$/24 hr., more preferably at least 2000 g/m$^2$/24 hr., and even more preferably at least 3000 g/m$^2$/24 hr. In some embodiments, the backsheet may have a moisture vapor transmission rate of from 1000 to 6000 g/m$^2$/24 hr. or any individual number within the range. Some breathable backsheet materials are described in greater detail in PCT Application No. WO 95/16746; U.S. Pat. Nos. 5,938,648; 5,865,823; and 5,571,096. Other suitable exemplary materials and a suitable test method for measuring the MVTR is described in U.S. Pat. No. 6,448,467.

Any suitable material can be used for the sensation member. Some examples of suitable materials include nonwovens, foams, woven materials, etc. For example, the sensation member may comprise rayon, Lyocell and other cellulose-based materials, cotton, polyester, polypropylene and polypropylene blends (e.g., with other listed materials, such as a Lyocell/polypropylene blend), and hydrophilic forms of nonwovens such as SM (spunbond meltblown), SMS (spunbond meltblown spunbond), and SMMS (spunbond meltblown meltblown spunbond). Other examples of suitable materials include 10 gsm SSMMS polypropylene; a Lyocell/polypropylene blend with 5-25% Lyocell/75-95% polypropylene. In specific embodiments, the Lyocell/polypropylene blend can be a nonwoven web having a basis weight of about 25 gsm and two layers. The A first layer may be a 15 gsm hydrophilic carded layer having 12 gsm polypropylene and 3 gsm Lyocell, and a second layer may be a 10 gsm hydrophobic spunbond polypropylene layer joined to the 15 gsm carded layer).

The sensation member may comprise any suitable basis weight. In some embodiments, the basis weight of the sensation member can be between about 10 to about 35 gsm or any individual number within the range. Additionally, the sensation members of the present invention may comprise any suitable bulk density. For example, in some embodiments, the bulk density can be between about 0.06 g/cm$^3$ to about 0.15 g/cm$^3$ or any individual number within the range.

In addition to the features described above, the disposable absorbent article 20 may also include a variety of features known in the art, such as slit openings, outer leg cuffs, front and rear ear panels, waist cap features, elastics, and the like to provide desired fit, containment, and aesthetic characteristics. Such additional features are well known in the art and are described in U.S. Pat. Nos. 3,860,003; 4,515,595; 5,151,092; 5,221,274; 5,518,801; and 6,482,191, among others.

Some examples of suitable topsheets are described further in U.S. Pat. Nos. 3,929,135; 4,324,246; 4,342,314; 4,463,045; 5,006,394; 4,609,518; 4,629,643. Any portion of the topsheet may be coated with a lotion as is known in the art. Examples of suitable lotions include those described in U.S. Pat. Nos. 5,607,760; 5,609,587; 5,635,191; 5,643,588; 5,968,025; 6,716,441; and PCT Publication No. WO 95/24173. Further, as mentioned previously, the topsheet may be fully or partially elasticated or may be foreshortened so as to provide a void space between the topsheet and the absorbent core.

An example of a suitable backsheet for use in the disposable absorbent article of the present invention may be impervious to liquids (e.g., urine) and comprise a thin plastic film such as a thermoplastic film having a thickness, for example, of about 0.012 mm (0.5 mil) to about 0.051 mm (2.0 mils). Suitable backsheet films include those manufactured by Tredegar Corporation, based in Richmond, Va., and sold under the trade name CPC2 film. Other suitable backsheet materials may include breathable materials which permit vapors to escape from the pull-on garment while still preventing exudates from passing through the backsheet. Suitable breathable materials may include materials such as woven webs, nonwoven webs, composite materials such as film-coated nonwoven webs, microporous films such as manufactured by Mitsui Toatsu Co., of Japan under the designation ESPOIR NO and by Tredegar Corporation of Richmond, Va. and sold under the designation EXAIRE, and monolithic films such as manufactured by Clopay Corporation, Cincinnati, Ohio under the name HYTREL blend P18-3097. Some breathable composite materials are described in greater detail in PCT Application No. WO 95/16746; U.S. Pat. Nos. 5,938,648; 5,865,823; and 5,571,096.

A suitable absorbent core for use in the present invention may comprise any absorbent material which is generally compressible, conformable, non-irritating to the wearer's skin, and capable of absorbing and retaining liquids such as urine and other certain body exudates. In addition, the configuration and construction of the absorbent core may also be varied (e.g., the absorbent core(s) or other absorbent structure (s) may have varying caliper zones, hydrophilic gradient(s), a superabsorbent gradient(s), or lower average density and lower average basis weight acquisition zones; or may comprise one or more layers or structures). Suitable absorbent structures for use as the absorbent core are described in U.S. Pat. Nos. 4,610,678; 4,673,402; 4,834,735; 4,888,231; 5,137,537; 5,147,345; 5,342,338; 5,260,345; 5,387,207; and 5,625,222. In some embodiments, the absorbent core may comprise a fluid acquisition component, a fluid distribution component, and a fluid storage component. An example of a suitable absorbent core having a fluid acquisition component, a fluid distribution component, and a fluid storage component is described in U.S. Pat. No. 6,590,136.

Figure 11:
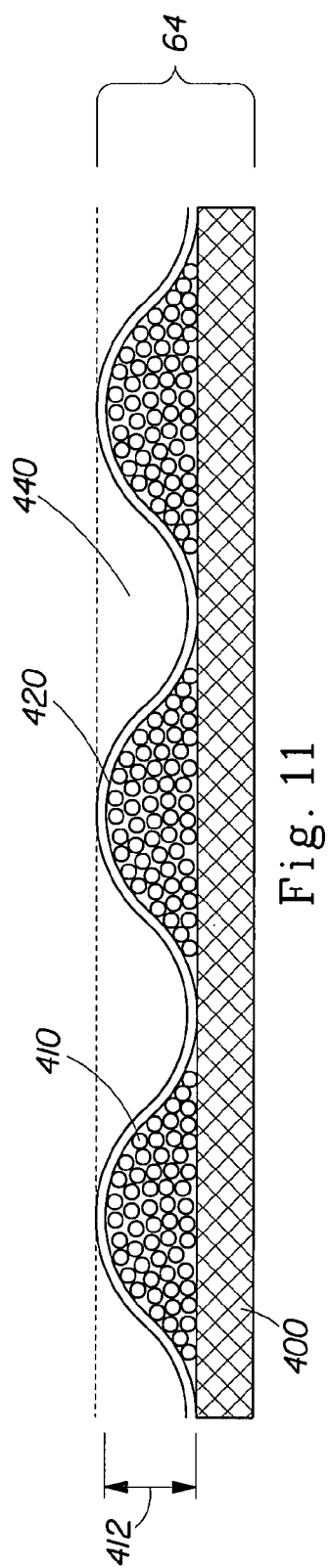
FIG. 11 is a cross-sectional view of a preferred embodiment of the absorbent core.

One preferred embodiment of the present invention includes, but is not limited to, articles described in U.S. Patent Application Ser. No. 2004/0162536 and U.S. Patent Application No. 2004/0167486. The aforementioned applications are directed to absorbent articles having an absorbent core which imparts increased wearing comfort to the article and makes it thin and dry. As shown in FIG. 11, the absorbent articles of the present invention may comprise an absorbent core 64 comprising a substrate layer 400, absorbent polymer material 410 and a fibrous layer of adhesive 420. The substrate layer 400 is preferably provided from a non-woven material, preferred non-wovens include those provided from synthetic fibers, such as PE, PET and PP. As the polymers used for non-woven production are inherently hydrophobic, they are preferably coated with hydrophilic coatings.

In accordance with the present invention, the absorbent material is immobilized when wet such that the absorbent core achieves a wet immobilization of more than 50%, preferably of more than 60%, 70%, 80% or 90%.

The substrate layer 400 comprises a first surface and a second surface. At least portions of the first surface of the substrate layer 400 are in direct contact with a layer of absorbent polymer material 410. This layer of absorbent polymer material 410 is preferably a discontinuous layer, and comprises a first surface and a second surface. As used herein, a discontinuous layer is a layer comprising openings. Typically, these openings have a diameter or largest span of less than 10 mm, preferably less than 5 mm, 3 mm, 2 mm and a span of more than 0.5 mm, 1 mm or 1.5 mm. At least portions of the second surface of the absorbent polymer material layer 410 are in contact with at least portions of the first surface of the substrate layer material 400. The first surface of the absorbent polymer material 410 defines a certain height 412 of the layer of absorbent polymer above the first surface of the layer of substrate material 400. When the absorbent polymer material layer 410 is provided as a discontinuous layer, portions of the first surface of the substrate layer 400 are not covered by absorbent polymer material 410. The absorbent core 64 further comprises a thermoplastic composition 420. This thermoplastic composition 420 serves to at least partially immobilize the absorbent polymer material 410.

In one preferred embodiment of the present invention the thermoplastic composition 420 can be disposed essentially uniformly within the polymeric absorbent material 410.

However, in an even more preferred embodiment of the present invention the thermoplastic material 420 is provided as a fibrous layer which is partially in contact with the absorbent polymer material 410 and partially in contact with the substrate layer 400. In this preferred structure the absorbent polymer material layer 410 is provided as a discontinuous layer, a layer of fibrous thermoplastic material 420 is laid down onto the layer of absorbent polymeric material 410, such that the thermoplastic layer 420 is in direct contact with the first surface of the layer of absorbent polymer material 410, but also in direct contact with the first surface of the substrate layer 400, where the substrate layer is not covered by the absorbent polymeric material 410. This imparts an essentially three-dimensional structure to the fibrous layer of thermoplastic material 420 which in itself is essentially a two-dimensional structure of relatively small thickness (in z-direction), as compared to the extension in x- and y-direction. In other words, the fibrous thermoplastic material layer 420 undulates between the first surface of the absorbent polymer material 410 and the first surface of the substrate layer 400.

Thereby, the thermoplastic material 420 provides cavities to hold the absorbent polymer material 410, and thereby immobilizes this material. In a further aspect, the thermoplastic material 420 bonds to the substrate 400 and thus affixes the absorbent polymer material 410 to the substrate 400. Highly preferred thermoplastic materials will also penetrate into both the absorbent polymer material 410 and the substrate layer 400, thus providing for further immobilization and affixation.

Of course, while the thermoplastic materials disclosed herein provide a much improved wet immobilization (i.e., immobilization of absorbent material when the article is wet or at least partially loaded), these thermoplastic materials also provide a very good immobilization of absorbent material when the article is dry.

In accordance with the present invention, the absorbent polymer material 410 may also be mixed with absorbent fibrous material, such as airfelt material, which can provide a matrix for further immobilization of the super-absorbent polymer material. However, preferably a relatively low amount of fibrous cellulose material is used, preferably less than 40 weight %, 20 weight %, or 10 weight % of cellulose fibrous material as compared to the weight of absorbent polymer material 410. Substantially airfelt free cores are preferred. As used herein, the term "absorbent fibrous material" is not meant to refer to any thermoplastic material 420 even if such thermoplastic material is fiberized and partially absorbent.

The absorbent core of the present invention may further comprise a cover layer. This cover layer may be provided of the same material as the substrate layer 400, or may be provided from a different material. Preferred materials for the cover layer are the non-woven materials. In this embodiment, portions of the cover layer bond to portions of the substrate layer 400 via the thermoplastic material 420. Thereby, the substrate layer 400 together with the cover layer provides cavities to immobilize the absorbent polymer material 410.

The areas of direct contact between the thermoplastic material 420 and the substrate material 400 are referred to as areas of junction 440. The shape, number, and disposition of the areas of junction 440 will influence the immobilization of the absorbent polymer material 410. The areas of junction can be of squared, rectangular, or circular shape. Preferred areas of junction are of circular shape. Preferably, they have a diameter of more than 0.5 mm, or 1 mm, or 1.5 mm and of less than 10 mm, or 5 mm, or 3 mm, or 2 mm. If the areas of junction 440 are not of circular shape, they preferably are of a size as to fit inside a circle of any of the preferred diameters given above.

The areas of junction 440 can be disposed in a regular or irregular pattern. For example, the areas of junction 440 may be disposed along lines. These lines may be aligned with the longitudinal axis of the absorbent core, or alternatively, they may have a certain angle in respect to the longitudinal edges of the core. It has been found, that a disposition along lines parallel with the longitudinal edges of the absorbent core 64 create channels in the longitudinal direction which lead to a lesser wet immobilization. Preferably, therefore the areas of junction 440 are arranged along lines which form an angle of 20 degree, 30 degree, 40 degree, or 45 degree with the longitudinal edges of the absorbent core 64. Another preferred pattern for the areas of junction 440 is a pattern comprising polygons, for example pentagons and hexagons or a combination of pentagons and hexagons. Also preferred are irregular patterns of areas of junction 440, which also have been found to give a good wet immobilization.

Two fundamentally different patterns of areas of junctions 440 can be chosen in accordance with the present invention. In one embodiment, the areas of junctions are discrete. They are positioned within the areas of absorbent material, like islands in a sea. The areas of absorbent materials are then referred to as connected areas. In an alternative embodiment, the areas of junctions can be connected. Then, the absorbent material can be deposited in a discrete pattern, or in other words the absorbent material represents islands in a sea of thermoplastic material 420. Hence, a discontinuous layer of absorbent polymer material 410 may comprise connected areas of absorbent polymer material 410 or may comprise discrete areas of absorbent polymer material 410.

In a further aspect of the present invention, it has been found that absorbent cores providing for a good wet immobilization can be formed by combining two layers. In this embodiment, the absorbent core material comprises two substrate layers 400, two layers of absorbent polymer material 410 and two layers of fibrous thermoplastic materials 420. When two discontinuous layers of an absorbent polymer material 410 are used, they would be typically arranged in such a way that the absorbent polymer material of the one layer faces the areas of junction 440 of the other layer. In an alternative preferred embodiment, however, the areas of junction 440 are offset and do not face each other.

According to the present invention, the thermoplastic layer 420 can comprise any thermoplastic composition, preferred are adhesive thermoplastic compositions, also referred to as hot melt adhesives. A variety of thermoplastic compositions are suitable to immobilize absorbent material. Some initially thermoplastic materials may later lose their thermoplasticity due to a curing step, e.g., initiated via heat, UV radiation, electron beam exposure or moisture or other means of curing, leading to the irreversible formation of a crosslinked network of covalent bonds. Those materials having lost their initial thermoplastic behaviour are herein also understood as thermoplastic materials 420.

The backsheet may be attached to the topsheet, the absorbent core, or any other element of the disposable absorbent article by any attachment means known in the art. For example, the attachment means may include a uniform continuous layer of adhesive, a patterned layer of adhesive, or an array of separate lines, spirals, or spots of adhesive. Some suitable attachment means are disclosed in U.S. Pat. Nos. 4,573,986; 3,911,173; 4,785,996; and 4,842,666. Examples of suitable adhesives are manufactured by H. B. Fuller Company of St. Paul, Minn. and marketed as HL-1620 and HL-1358-XZP. Alternatively, the attachment means may comprise heat bonds, pressure bonds, ultrasonic bonds, dynamic mechanical bonds, or any other suitable attachment means or combinations of these attachment means as are known in the art.

Examples of suitable configurations for leg cuffs are described in U.S. Pat. Nos. 3,860,003; 4,909,803; and 4,695,278.

In embodiments of the present disclosure, a disposable wearable absorbent article can include a stretchable outer cover. For example, the outer cover can be a uniaxially stretchable outer cover, configured to stretch in one direction. Also as an example, the outer cover can be a biaxially stretchable outer cover, configured to stretch in two directions. In various embodiments, the outer cover can be configured as described in U.S. non-provisional patent application entitled "Biaxially Stretchable Outer Cover for an Absorbent Article," filed on Nov. 15, 2006 with Express Mail No. EV916939625 and further identified by , which is hereby incorporated by reference.

In embodiments of the present disclosure, a disposable wearable absorbent can include an outer cover configured in various ways, including configurations of part or all of the outer cover as stretchable, non-stretchable, with an elastic nonwoven, with an elastic film and extensible nonwoven, with an extensible film and an elastic nonwoven, pre-stretched with elastic strands allowed to contract, mechanically activated, with zero strain laminate, and/or combinations of these and any other outer cover configurations. In various embodiments of the present disclosure, a disposable wearable absorbent article can include a printed outer cover with various basis weights, chemistries, and/or mechanical activations, as will be understood by one of ordinary skill in the art.

Test Methods:
Sample Preparation:
1. Enough representative absorbent articles are selected from the retail packaging of the absorbent article to conduct all required tests.
2. All of the steps involved in the sample preparation and the testing of the samples, unless otherwise noted, are performed in a controlled environment of 23.0° C.±1.0° C. and a relative humidity of 50%±2.0%. All samples prepared are allowed to equilibrate in this controlled environment of a period of 24 hours prior to testing.
3. Where noted, testing may require the disassembly of an absorbent article to test specific features. Where disassembly is required, the article is disassembled in a manner that minimally disturbs the structure of any layers comprising the absorbent article. For example, adhesively joined layers can be separated by first freezing them using a freeze spray such as Freeze-It® as is available from ITW Chemtronics Americas of Kennesaw, Ga. or Quick-Freeze™ available from Miller-Stephenson, Danbury Conn. Other samples may need to be cut from the absorbent article.
4. It shall be understood that the sensation member may also include components that are not necessarily part of the sensation member that is capable of contacting the skin of the wearer but that contributes to the delivery of a signal to the wearer. For example, a sample of a sensation member comprising a body contacting layer and a patch of material (including a sensation agent) attached to and located underneath the garment facing surface of the body contacting layer, will also include the patch of material. However, it will be also understood that a sensation member does not include other components of the article that are not contributing to the delivery of a feedback response to the wearer (for example, the absorbent core that may include a fluid acquisition component, a fluid distribution component, and/or a fluid storage component. An example of a suitable absorbent core having a fluid acquisition component, a fluid distribution component, and a fluid storage component is described in U.S. Pat. No. 6,590,136 to Young et al., issued Jul. 8, 2003 and assigned to The Procter & Gamble Company.).

Wicking Factor:
1. Remove the sensation member from the disposable article.
2. Subject the removed sensation member to the test method described in EDANA 10.4-02.

Absorptive Capacity:
1. Remove the sensation member from the disposable article.
2. Subject the removed sensation member to the test method described in EDANA 10.4-02.

Figure 12:
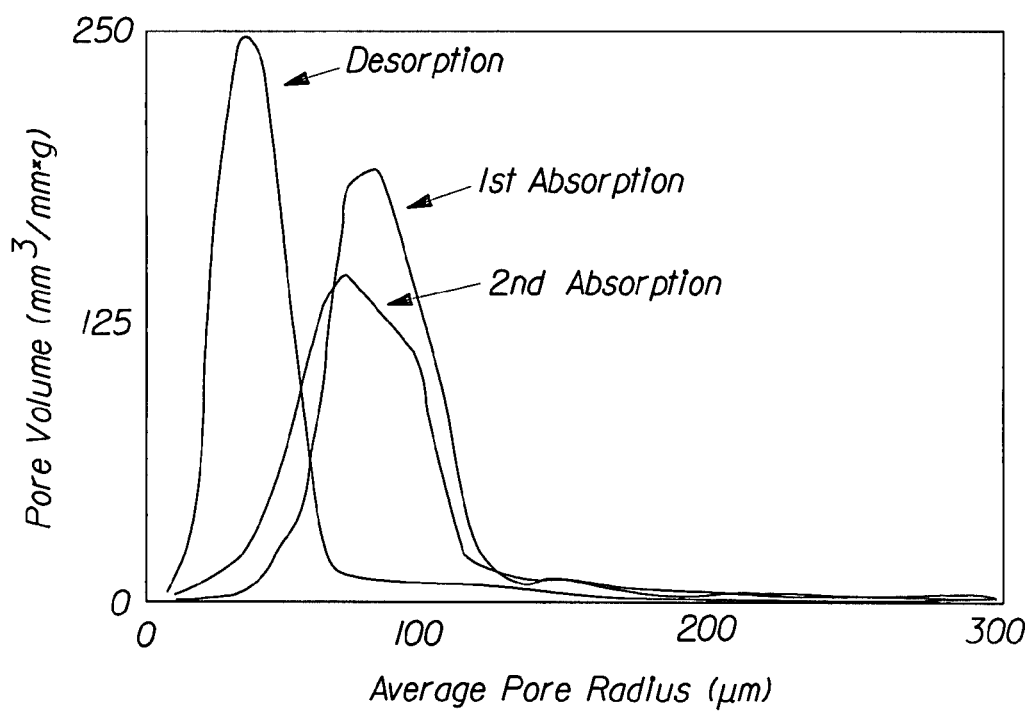
FIG. 12 is a graph showing exemplary curves for pore volume versus average pore radius.
Figure 13:
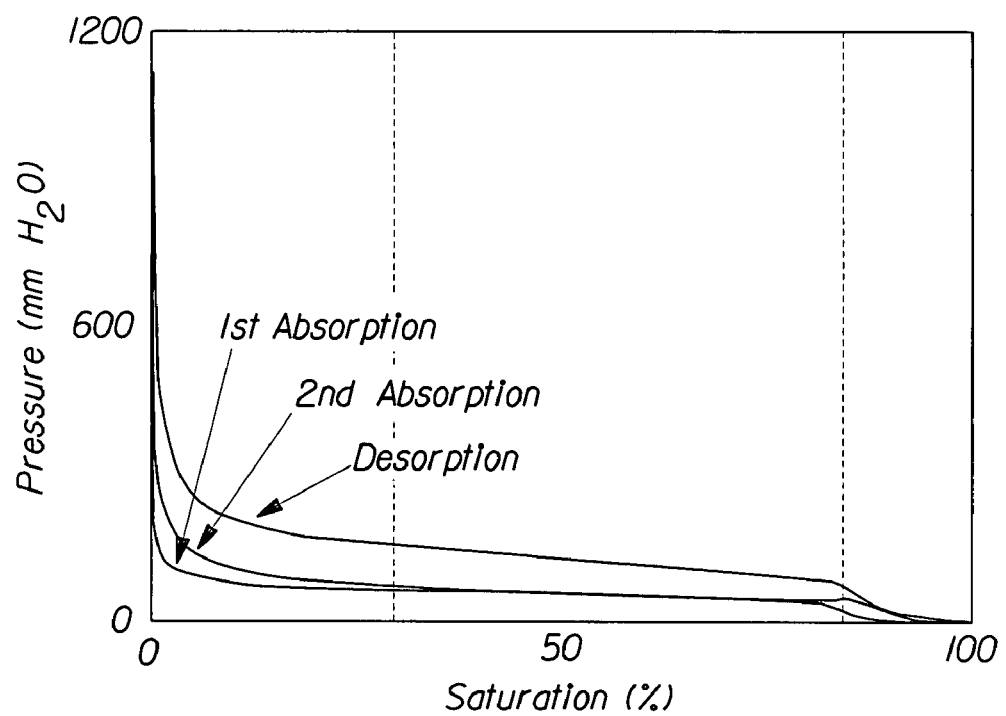
FIG. 13 is a graph showing exemplary curves for pressure versus saturation.

Capillary Pressure:
1. Remove the sensation member from the disposable article.
2. Pore volume distribution and capillary pressure are measured with a TRI Autoporosimeter using their ACK21 software (available from TRI/Princeton, Princeton, N.J.). The instrument is set up and operated in accordance to the standard procedures defined by TRI.
3. Measurements are performed on an initially dry sensation member using hexadecane and a 0.20 psi confining pressure during an absorption, desorption, and second absorption cycle.
4. Pores between 5 □m and 1200 □m are measured.
5. Prepare a 0.65 □m filter paper (Millipore, Billerica Mass.) by first cleaning the porous metal plate with acetone and then adhering the paper to the plate with white KRYLON® spray paint.
5. The chamber is set to the minimal height required to maintain proper mass balance between the fluid reservoir and the surface of the filter paper on the frit surface.
6. The sensation member is cut to a 5.4 mm by 5.4 mm square. The midpoint of the square is located at follows: for gender specific absorbent articles—(boy) 10.2 cm below front edge of the core; (girl) 12.7 cm below front edge of the core; for gender neutral (unisex or generic) 10.2 cm below the front edge of the core.
7. Measure both the weight and caliper (at 0.1 psi) of the sample.
8. Place cover plate and weight into the empty sample chamber, close the chamber. After the instrument's internal caliper gauge is set to zero, open the chamber and remove the cover plate. Close the chamber. After the instrument has applied the appropriate air pressure to the cell to achieve the 5 mm pore radius, close the liquid valve. Open the sample chamber, place the specimen, cover plate and confining weight into the chamber and close it. Open liquid valve to allow free movement of liquid to the balance and begin the test. The instrument will proceed through one absorption/desorption/absorption cycle. A blank (without specimen) is run in like fashion.
9. Based on the incremental volume values, the calculations program calculates blank-corrected values for cumulative volume versus equivalent pore radius. Cumulative volumes are divided by the dry weight of the specimen. Cumulative volumes are divided by the volume at saturation (i.e., the cumulative volume measured for the largest equivalent radius at zero or near-zero pressure) to obtain the normalized cumulative volume (expressed as %) versus equivalent pore radius. Examples of the calculated pore volume distribution and capillary pressure verses saturation curves are shown in FIG. 12 and FIG. 13.

Wetness Density Test
Purpose: This test simulates the introduction of urine into a training pant diaper.

| Supplies and Equipment | |
|---|---|
| Template | Curved Base unit on which to mount the test product |
| Filter Paper | Alhstrom Filtration Paper Code 632, 5 × 5 in |
| Balance | Accuracy +/−0.01 g |
| Timer | Convenient Source, measurements taken to nearest second |
| Fluid Delivery System | Erlynmeyer flask or other Convenient Source |
| Saline | 0.9% Saline heated to 37° C. +/− 1° C. |
| Resin Blocks | 0.025 PSI +/− 0.001 PSI, 5 × 5 in |
| Ruler | Convenient Source, measurement taken to 0.1 in |
| Marker pen | Convenient Source |

Test Procedure
1. Open side seams of all products being tested.
2. Place a mark on the topsheet designating the typical voiding point and loading point for the saline.
   a. Boy: Size 5 (3T/4T) 4.5 inches below front top edge of the core and centered between barrier leg cuffs
   b. Girl: Size 5 (3T/4T) 5.5 inches below front top edge of the core and centered between barrier leg cuffs
3. Measure mark on the diaper for placement of the filter paper. Measure 3 inches from the front top edge of core and place a mark.
4. Snip the cuffs to relax them at the 3 inch mark in the front and approximately the same distance from the back.
5. Mount the training pant onto the curved base unit with the topsheet side facing up. The cuffs should be pulled out and clear of the topsheet.
6. Weigh two pieces of filter paper.
7. Measure 75 mls of saline (representing a single load).
8. Pour the saline into the pant at loading point at a rate of about 15 mi/sec (5 seconds for 75 ml).
9. As soon as all of the fluid enters the diaper, immediately start the timer for the desired time (30 seconds, 1 min., etc.).
10. After the designated time has elapsed, place the two pieces of pre-weighed filter paper side by side on the diaper. Immediately and gently place one block on top of each piece of filter paper.
11. Set timer for 15 seconds.
12. At the end of the 15 seconds remove the blocks and weigh the filter paper.
13. Calculate wet filter paper weight minus dry filter paper weight.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article having a waist region and a crotch region, the article comprising:
   a backsheet;
   an absorbent core disposed in a face-to-face orientation with the backsheet; and
   a liquid pervious topsheet comprising a sensation member, which forms a portion of a wearer-facing surface of the absorbent article, wherein the sensation member is configured to provide a feedback response to a wearer of the absorbent article after occurrence of a urination event, and wherein the sensation member has a wicking factor of greater than about 20 mm at about one minute, an absorptive capacity of greater than about 0.01 g/cm$^2$, and a capillary pressure of greater than about 50 mm of water;
   wherein the sensation member has a first WD at about 60 seconds and a second WD at about 10 minutes, wherein the second WD is less than 80% of the first WD, and wherein the second WD is greater than 0.

2. The absorbent article of claim 1, wherein the sensation member has an absorptive capacity of greater than about 0.08 g/cm$^2$.

3. The absorbent article of claim 1, wherein the sensation member has a capillary pressure of less than about 500 mm of water.

4. The absorbent article of claim 1, wherein the sensation member has a wicking factor of between about 20 mm at about one minute and about 100 mm at about one minute, an absorptive capacity of between about 0.01 g/cm$^2$ and about 0.14 g/cm$^2$, and a capillary pressure of greater than about 100 mm of water.

5. The absorbent article of claim 1, wherein the topsheet is joined to at least a portion of the backsheet, wherein the absorbent core is disposed between the topsheet and the backsheet, and wherein the sensation member is disposed superjacent to the topsheet.

6. The absorbent article of claim 1, wherein the sensation member has a WD of greater than 1.2 mg/cm$^2$ at about 60 seconds.

7. The absorbent article of claim 1, wherein the sensation member has a WD of between about 1.2 mg/cm$^2$ to about 5 mg/cm$^2$ at about 60 seconds.

8. The absorbent article of claim 1, wherein the sensation member has a WD of less than about 3 mg/cm$^2$ at about 60 minutes.

9. The absorbent article of claim 1, wherein the sensation member has a WD of between about 0.5 mg/cm$^2$ to about 3 mg/cm$^2$ at about 60 minutes.

10. The absorbent article of claim 1, wherein the sensation member has a WD of less than about 4.7 mg/cm$^2$ at about 10 minutes.

11. The absorbent article of claim 1, wherein the sensation member has a WD of between about 0.5 mg/cm$^2$ to about 4.7 mg/cm$^2$ at about 10 minutes.

12. The absorbent article of claim 1, wherein the sensation member comprises a treatment consisting of the following: hydrophobic coating, hydrophilic coating, mechanical treatment, zone coating, chemical treatment, and combinations thereof.

13. The absorbent article of claim 12, wherein the sensation member comprises a treatment which is integral with the sensation member.

14. The absorbent article of claim 12, wherein the sensation member comprises a separate layer which includes the treatment.

15. The absorbent article of claim 12, wherein the sensation member comprises treatment zones which extend in a direction generally parallel to a lateral axis of the sensation member.

16. The absorbent article of claim 12, wherein the sensation member comprises treatment zones which extend in a direction generally parallel to a longitudinal axis of the sensation member.

17. The absorbent article of claim 15, wherein at least one of the treatment zones is mechanically treated.

18. The absorbent article of claim 16, wherein at least one of the treatment zones is chemically treated.

19. A disposable diaper for wearing about a lower torso of a wearer, the disposable diaper comprising a first waist region disposed adjacent to a first waist edge, a second waist region disposed adjacent to a second waist edge, a crotch region disposed between the first waist region and the second waist region, a first longitudinal edge, and a second longitudinal edge, the disposable diaper comprising:
   a topsheet;
   a backsheet joined to at least a portion of the topsheet;
   an absorbent core disposed between the topsheet and the backsheet;
   a first side panel extending outward from the first longitudinal edge in the first waist region and a second side panel extending outward from the second longitudinal edge in the first waist region, wherein the first side panel and the second side panel are adaptable to engage the second waist region thereby forming a waist opening and a pair of leg openings; and
   a sensation member disposed on top of the topsheet, wherein the sensation member is in at least intermittent contact with the wearer's skin when the diaper is worn by the wearer, wherein the sensation member is configured to maintain at least some urine discharged by the wearer during a urination event in at least intermittent contact with the wearer's skin after the urination event to indicate the occurrence of the urination event to the wearer, and wherein the sensation member has a wicking factor of greater than about 20 mm at about one minute, an absorptive capacity of greater than about 0.01 g/cm$^2$, and a capillary pressure of greater than about 50 mm of water;
   wherein the sensation member has a first WD at about 60 seconds and a second WD at about 10 minutes, wherein the second WD is less than 80% of the first WD, and wherein the second WD is greater than 0.

20. The disposable diaper of claim 19, wherein the sensation member has an absorptive capacity of greater than about 0.08 g/cm$^2$.

21. The disposable diaper of claim 19, wherein the sensation member has a capillary pressure of less than about 500 mm of water.

22. The disposable diaper of claim 19, wherein the sensation member has a wicking factor of between about 20 mm at about one minute and about 100 mm at about one minute, an absorptive capacity of between about 0.01 g/cm$^2$ and about 0.14 g/cm$^2$, and a capillary pressure of greater than about 100 mm of water.

23. The disposable diaper of claim 19, wherein the sensation member has a WD of greater than 1.2 mg/cm$^2$ at about 60 seconds.

24. The disposable diaper of claim 19, wherein the sensation member has a WD of between about 1.2 mg/cm$^2$ to about 5 mg/cm$^2$ at about 60 seconds.

25. The disposable diaper of claim 19, wherein the sensation member has a WD of less than about 3 mg/cm$^2$ at about 60 minutes.

26. The disposable diaper of claim 19, wherein the sensation member has a WD of between about 0.5 mg/cm$^2$ to about 3 mg/cm$^2$ at about 60 minutes.

27. The disposable diaper of claim 19, wherein the sensation member has a WD of less than about 4.7 mg/cm$^2$ at about 10 minutes.

28. The disposable diaper of claim 19, wherein the sensation member has a WD of between about 0.5 mg/cm$^2$ to about 4.7 mg/cm$^2$ at about 10 minutes.

29. The absorbent article of claim 1, wherein the feedback response provided by the sensation member comprises a wetness signal.

30. The absorbent article of claim 1, wherein the feedback response provided by the sensation member comprises a temperature change in the sensation member relative to a temperature of the wearer's urine discharged during the urination event.

31. The absorbent article of claim 1, wherein the feedback response provided by the sensation member is a wetness signal and a temperature change.

* * * * *